(12) United States Patent
Yamamoto

(10) Patent No.: US 11,432,786 B2
(45) Date of Patent: Sep. 6, 2022

(54) X-RAY FLUOROSCOPIC IMAGING APPARATUS

(71) Applicant: Hitachi, Ltd., Tokyo (JP)

(72) Inventor: Kaoru Yamamoto, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 42 days.

(21) Appl. No.: 17/205,254

(22) Filed: Mar. 18, 2021

(65) Prior Publication Data

US 2022/0071581 A1 Mar. 10, 2022

(30) Foreign Application Priority Data

Sep. 4, 2020 (JP) .............................. JP2020-149145

(51) Int. Cl.
*A61B 6/00* (2006.01)

(52) U.S. Cl.
CPC ................ *A61B 6/487* (2013.01); *A61B 6/40* (2013.01); *A61B 6/4441* (2013.01); *A61B 6/54* (2013.01)

(58) Field of Classification Search
CPC ... A61B 6/4405; A61B 6/0407; A61B 6/4482; A61B 6/0428; A61B 6/46; A61B 6/4441; A61B 6/0487; A61B 6/501; A61B 6/40; A61B 6/487; A61B 6/04; A61G 2210/50; A61G 13/04; A61G 13/06; A61G 7/018
See application file for complete search history.

(56) References Cited

FOREIGN PATENT DOCUMENTS

| JP | 11-137540 A | 5/1999 | |
| JP | 2021097809 A | * 7/2021 | ............. A61B 6/107 |

\* cited by examiner

*Primary Examiner* — Don K Wong
(74) *Attorney, Agent, or Firm* — Mattingly & Malur, PC

(57) ABSTRACT

An X-ray fluoroscopic imaging apparatus includes first slide mechanism is disposed at a lower end of a support column, and a second slide mechanism is disposed at an upper end of the support column. When an operation unit has received an instruction, a controller performs a first mode in which the X-ray generator is moved in the predetermined direction by operating the second slide mechanism to move an X-ray support arm in the predetermined direction with respect to the upper end of the support column. Thereafter, the controller performs a second mode of operating the first slide mechanism to move the lower end of the support column at a predetermined first speed in the predetermined direction with respect to a support column support arm, while operating the second slide mechanism to move the X-ray support arm at a second speed smaller than the first speed in an opposite direction.

6 Claims, 17 Drawing Sheets

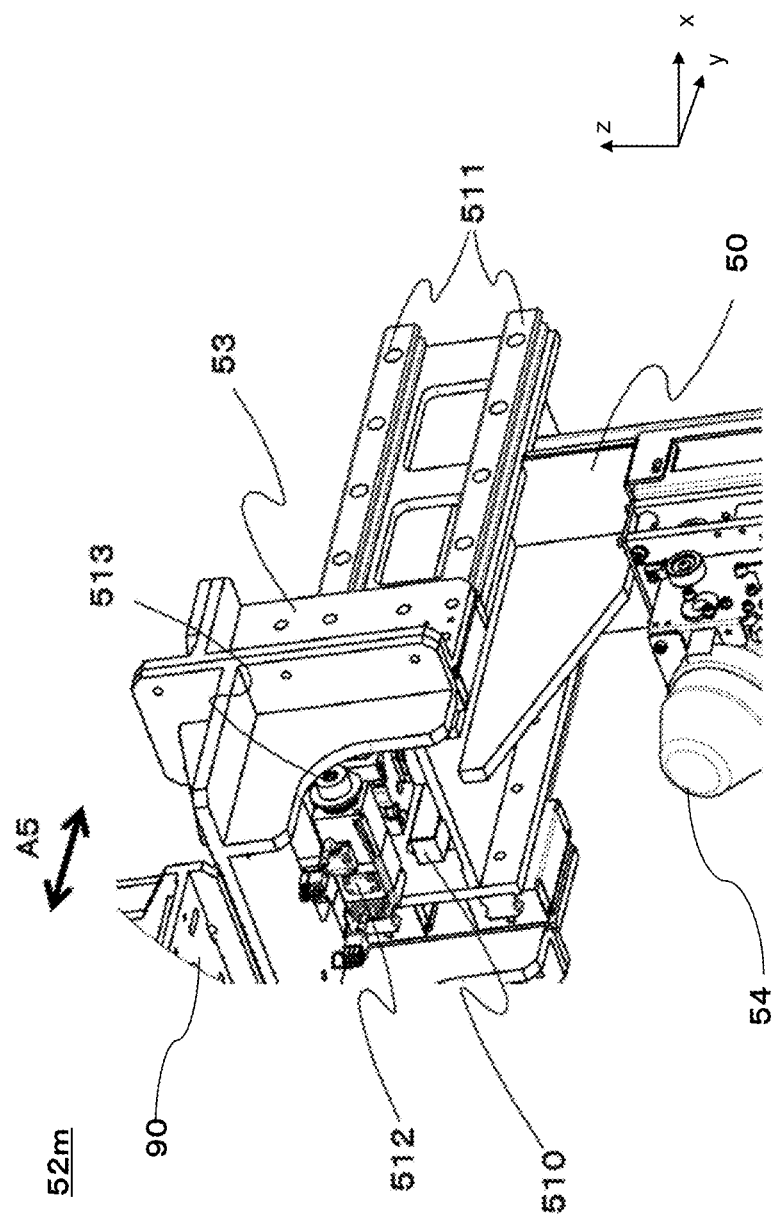

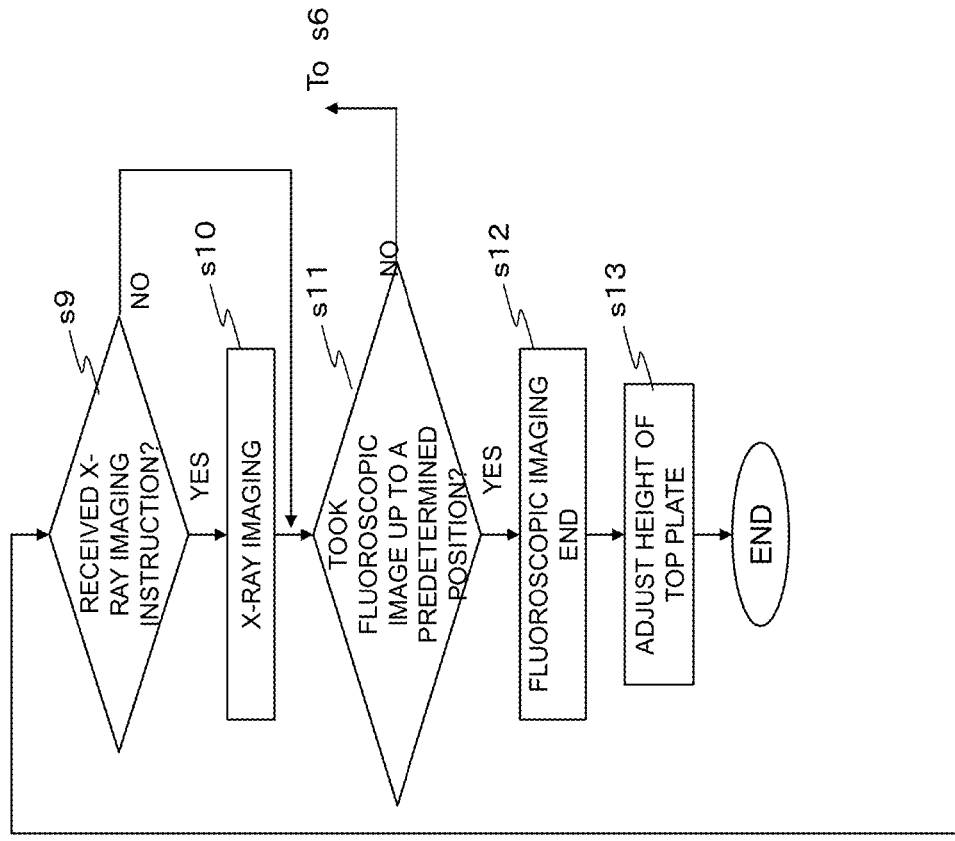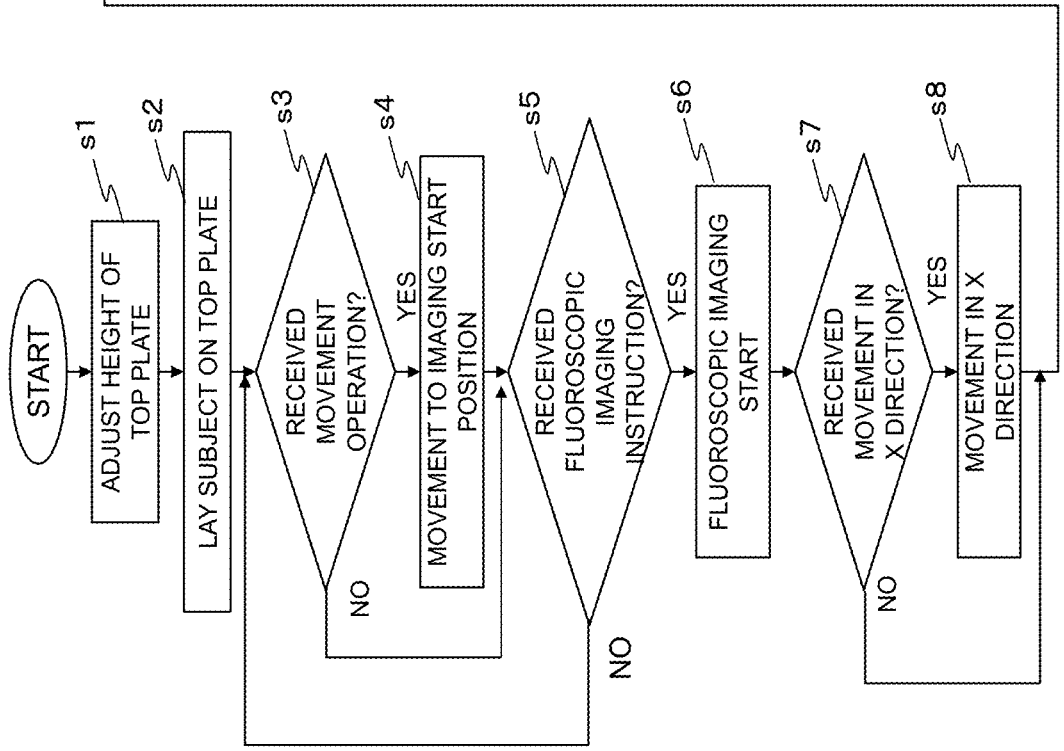

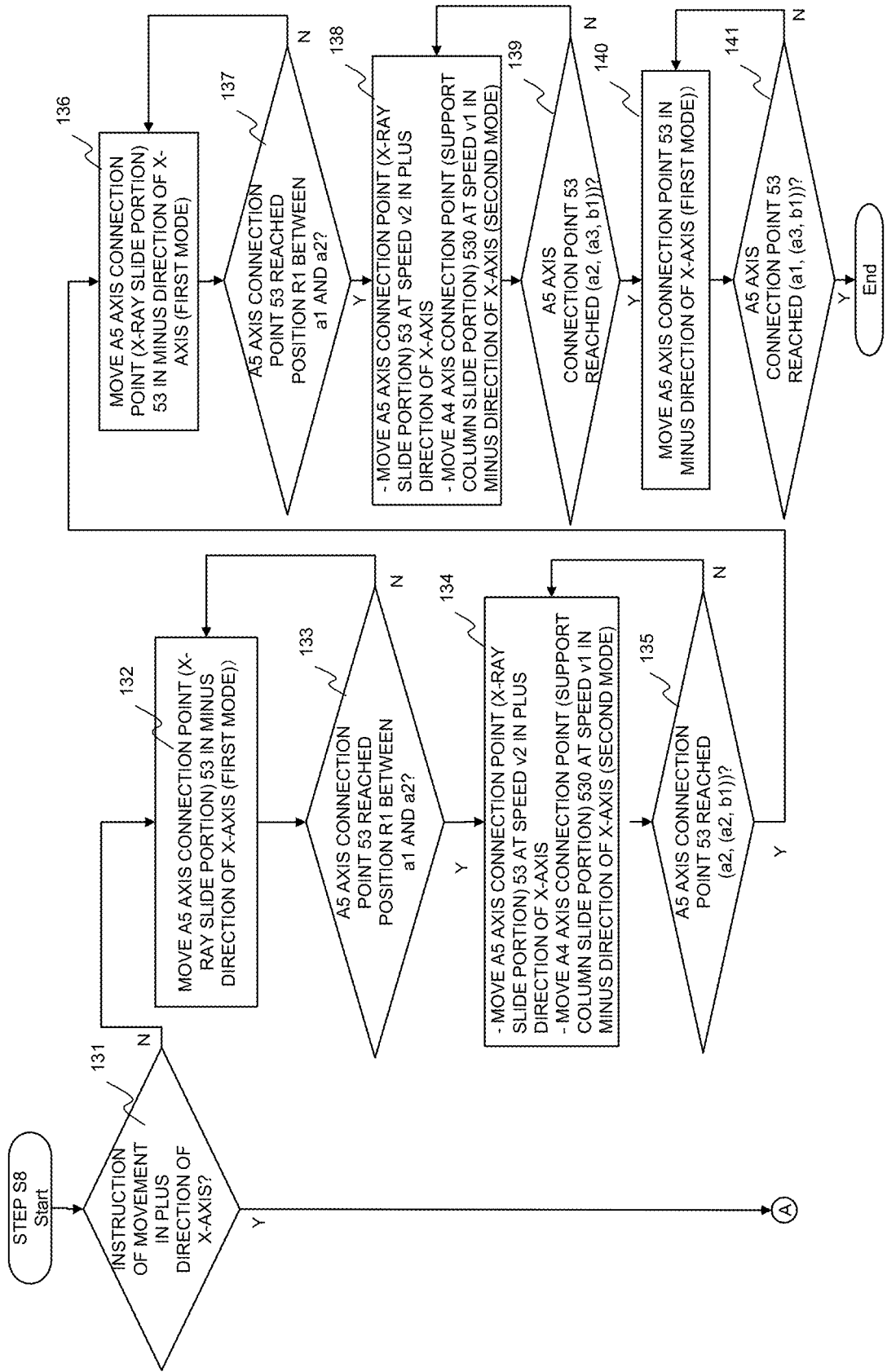

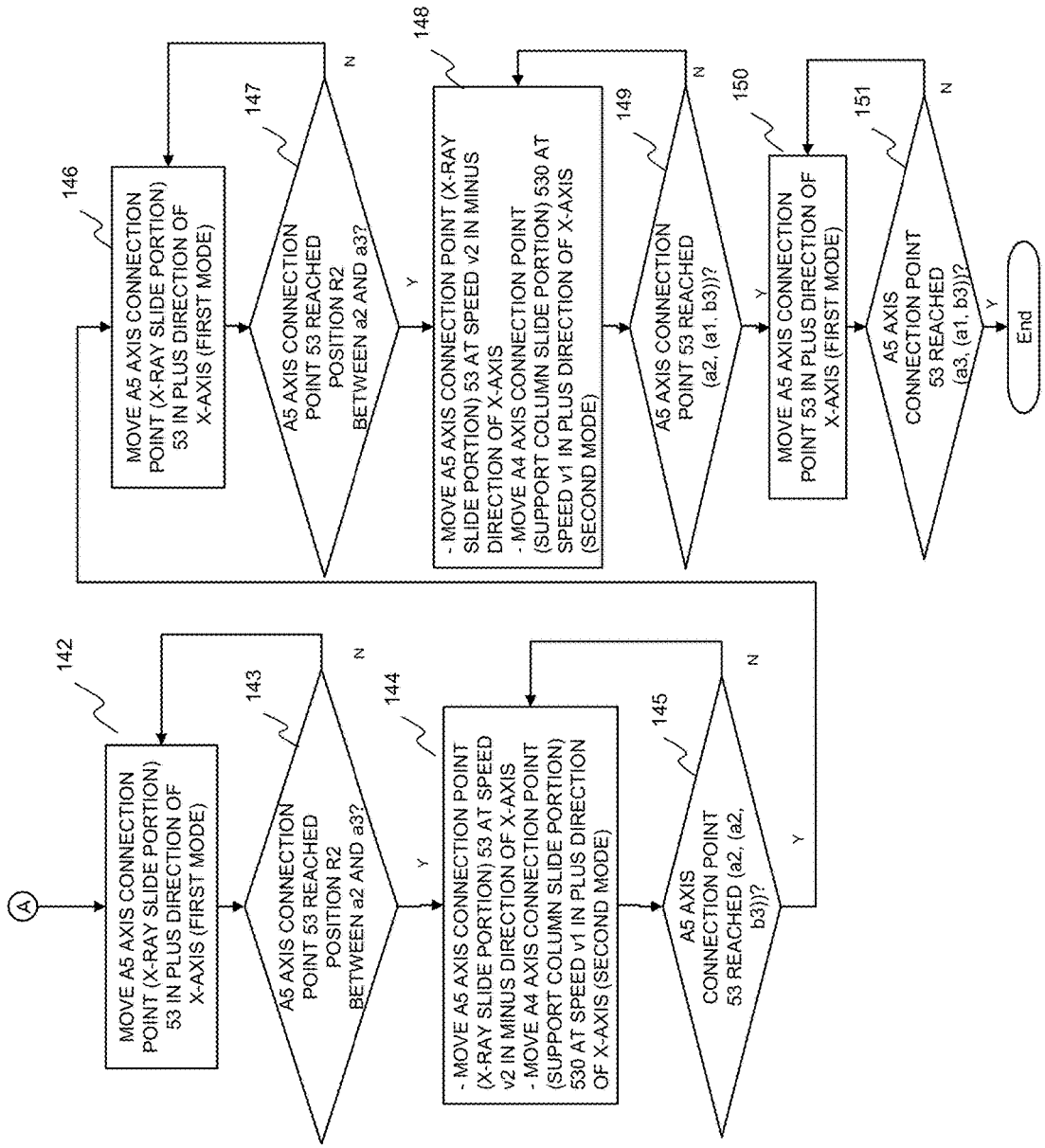

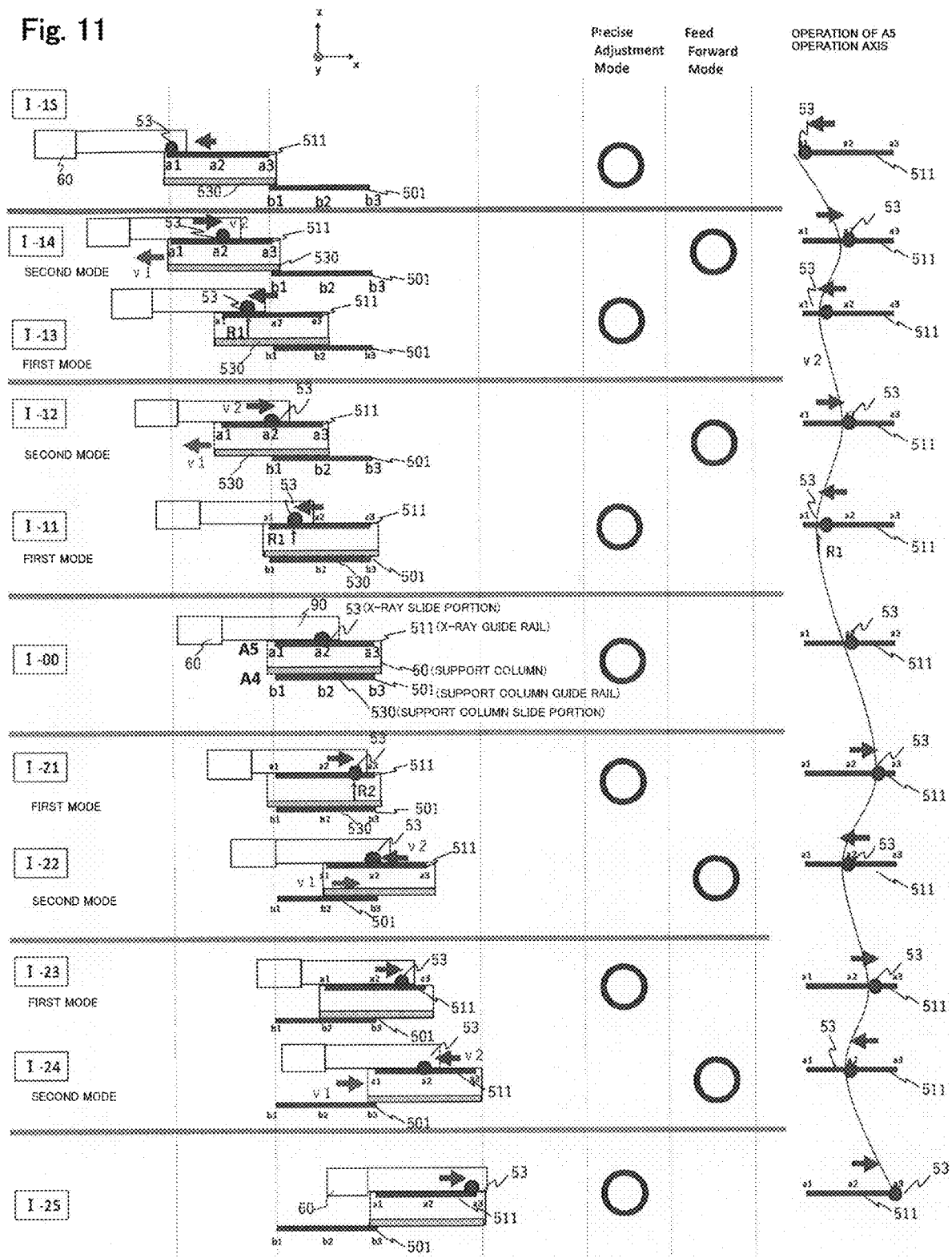

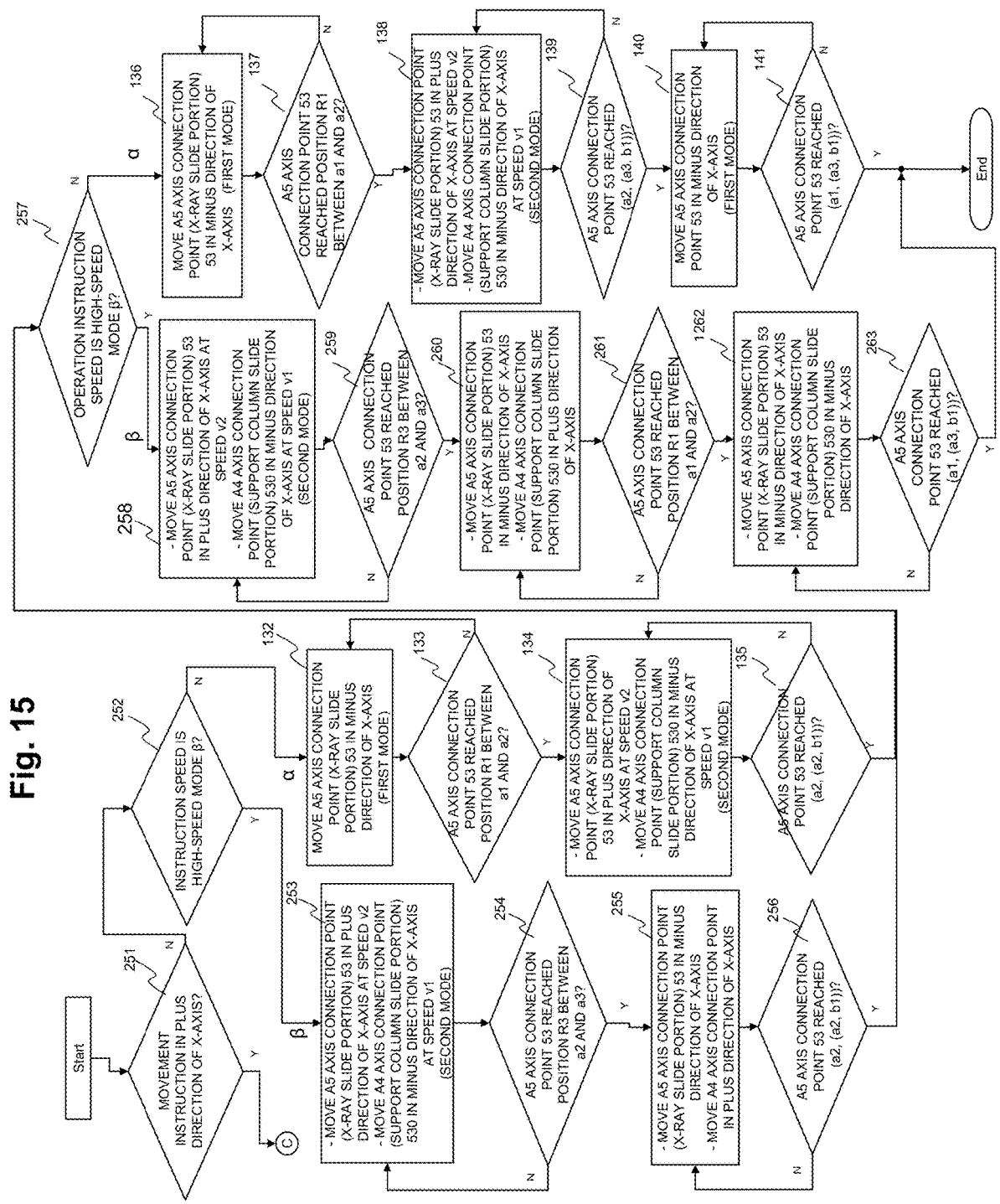

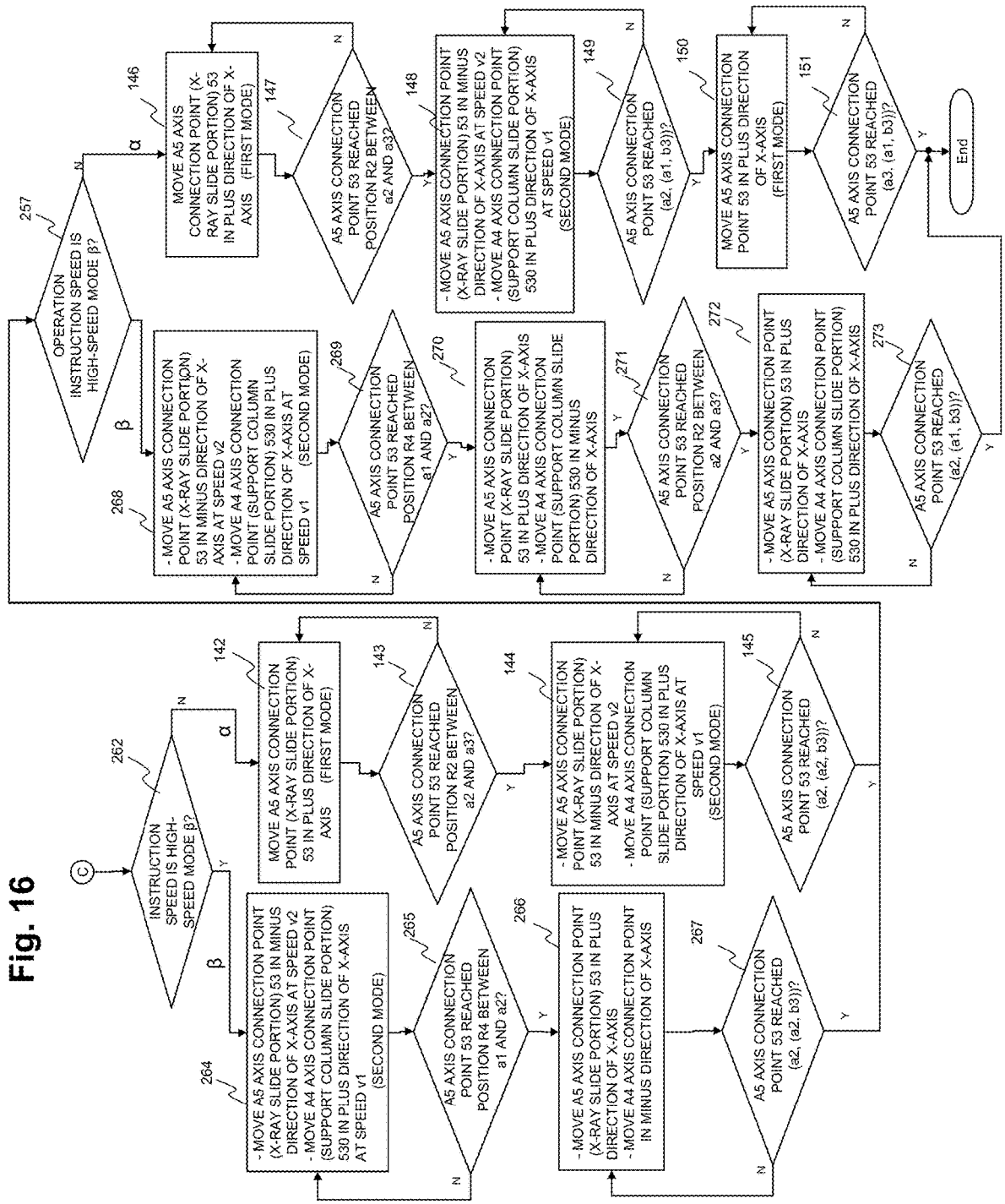

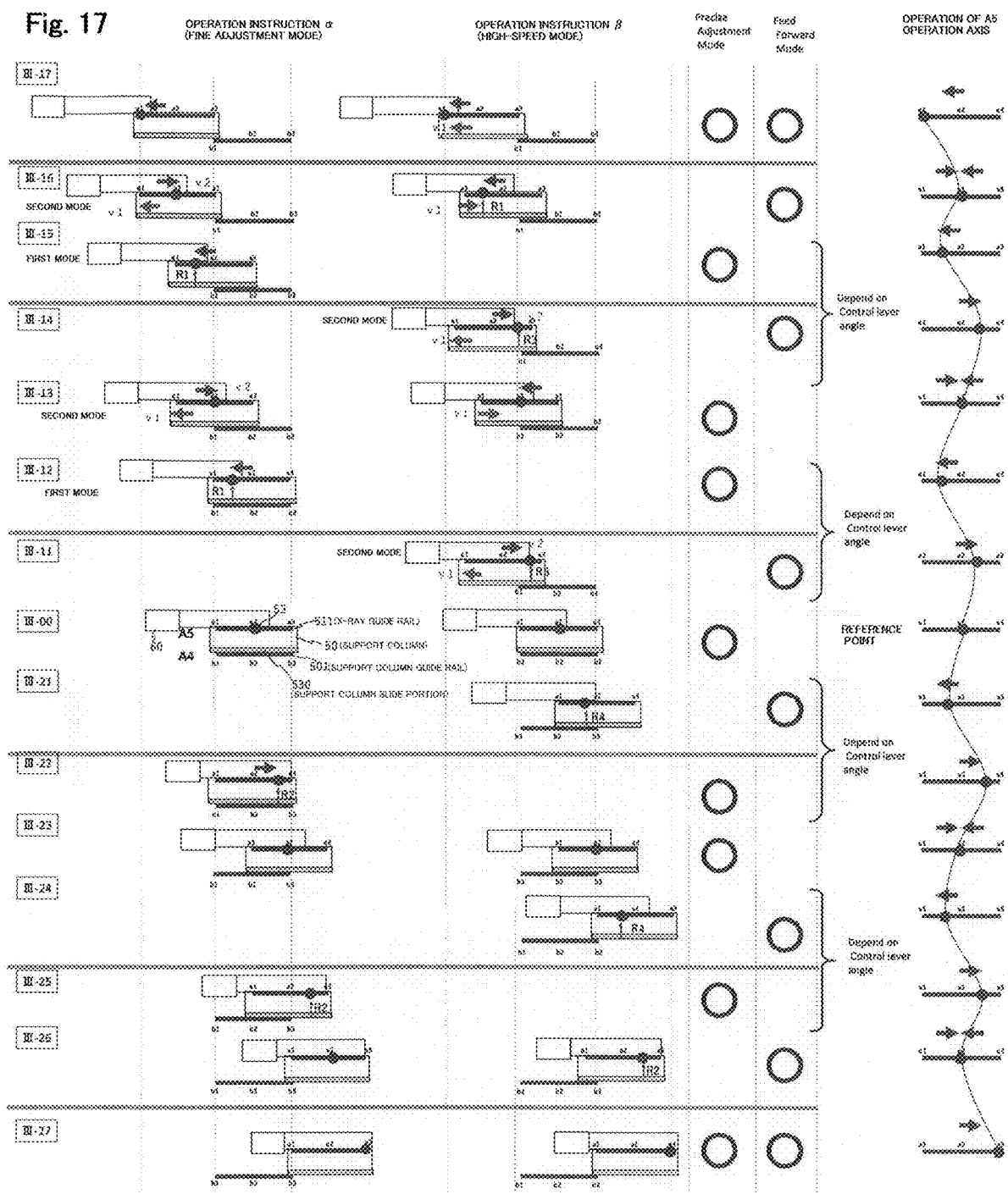

X-RAY FLUOROSCOPIC IMAGING APPARATUS

CROSS-REFERENCE TO RELATED APPLICATION

The present application claims priority from Japanese application JP2020-149145, filed on Sep. 4, 2020, the contents of which is hereby incorporated by reference into this application.

BACKGROUND OF THE INVENTION

Field of the Invention

The present invention relates to an X-ray fluoroscopic imaging apparatus for performing fluoroscopic imaging of a subject, and particularly to the X-ray fluoroscopic imaging apparatus suitable for Inter-Ventional Radiology (IVR).

Background Art

In recent years, in the IVR that performs a procedure while performing X-ray fluoroscopy on the subject, specifically in endoscopic retrograde cholangiopancreatography (ERCP) and endoscopic sphincterotomy (EST), the X-ray fluoroscopic imaging apparatus has come to be widely used.

In the IVR using an endoscope, since the procedure is performed while moving the endoscope inside the subject and checking its position, the X-ray fluoroscopic imaging apparatus having a configuration capable of changing an X-ray irradiation position (imaging position) on the subject during fluoroscopic imaging is desired.

Patent Literature 1 discloses an example of the X-ray fluoroscopic imaging apparatus capable of changing the imaging position during fluoroscopic imaging. In the X-ray fluoroscopic imaging apparatus, a top plate on which the subject is mounted can be slid together with a support frame of the top plate in a short axis direction and a long axis direction of the top plate, and a fluoroscopic imaging position of the subject can be changed while rotating an X-ray generator and an X-ray detector about an axis parallel to the short axis direction of the top plate (see FIG. 8 of JP-A-11-137540). Further, JP-A-11-137540 discloses an imaging method in which a stand supporting the X-ray generator and the support frame of the top plate is set upright, and an orientation of the X-ray generator is changed so that X-rays are emitted from the X-ray generator toward a floor surface, and the subject mounted on a stretcher is disposed between the X-ray generator and the floor surface (see (b) of FIG. 7 of JP-A-11-137540). In the latter imaging method, the X-ray generator can be moved horizontally to the floor surface, but a distance between the X-ray generator and the subject cannot be adjusted.

SUMMARY OF THE INVENTION

Technical Problem

However, in a conventional X-ray fluoroscopic imaging apparatus described in FIG. 8 or the like of JP-A-11-137540, when it is desired to move an X-ray irradiation range (a field of view) in the long axis direction and the short axis direction of the top plate during fluoroscopic imaging, a load may be applied to the subject on the top plate because the apparatus is configured to move (slide) the top plate. For example, when performing the IVR, the procedure of moving the endoscope in the subject while moving the subject into which the endoscope is inserted in the horizontal direction by moving the top plate is performed, and the load is large for both an operator and the subject.

On the other hand, as disclosed in (b) of FIG. 7 of JP-A-11-137540, it is conceivable to move the X-ray generator with respect to a support column, but the X-ray generator includes an X-ray tube, a diaphragm blade or the like inside thereof and is heavy. In a configuration in which a support position of the X-ray generator is slid or rotated as in the conventional X-ray fluoroscopic imaging apparatus, when the heavy X-ray generator is moved in a direction away from a stand portion fixed to the floor surface, the load applied to a movement mechanism of the support position is large, and it is not easy to move the X-ray generator in a stable posture. It is also possible to design the movement mechanism of the X-ray generator so that movement of the heavy X-ray generator can be started quickly and stopped accurately at a desired position, but in this case a structure of the movement mechanism is large, and a weight of a support mechanism of the X-ray generator is even larger.

SUMMARY OF INVENTION

An object of the present invention is to provide the X-ray fluoroscopic imaging apparatus capable of moving the X-ray generator quickly, smoothly, and over a wide range, and easily adjusting the field of view (X-ray irradiation range).

An X-ray fluoroscopic imaging apparatus of the present invention includes: a stand placed on a floor surface; a support column support arm projecting from one side of the stand in a predetermined direction; a support column having a lower end mounted on the support column support arm, and supported by the support column support arm; an X-ray support arm projecting from an upper end of the support column in a direction parallel to the predetermined direction; an X-ray generator supported by the X-ray support arm; a first slide mechanism that is disposed between the support column support arm and the lower end of the support column and slides the lower end of the support column parallel to the predetermined direction with respect to the support column support arm; a second slide mechanism that is disposed between the upper end of the support column and the X-ray support arm and slides the X-ray support arm parallel to the predetermined direction with respect to the upper end of the support column; a controller that controls operations of the first and second slide mechanisms; and an operation unit that receives an instruction from a user to move the X-ray generator in the predetermined direction. The controller performs the following first mode and second mode in order. In the first mode, when the operation unit has received the instruction from the user to move the X-ray generator in the predetermined direction, the controller operates the second slide mechanism to move the X-ray support arm in the predetermined direction with respect to the upper end of the support column, so that the X-ray generator is moved to the predetermined direction. In the second mode, the controller operates the first slide mechanism to move the lower end of the support column at a predetermined first speed in the predetermined direction with respect to the support column support arm, while operating the second slide mechanism to move the X-ray support arm at a second speed smaller than the first speed in a direction opposite to the predetermined direction with respect to the upper end of the support column, so that the X-ray generator is moved in the predetermined direction.

According to the present invention, it is possible to provide the X-ray fluoroscopic imaging apparatus capable of moving the X-ray generator quickly, smoothly, and over a wide range, and easily adjusting the field of view (X-ray irradiation range).

BRIEF DESCRIPTION OF THE DRAWINGS

FIG. 7 is a partial perspective view illustrating a configuration of a slide mechanism 52m;

FIG. 8 is a flowchart illustrating an operation of the X-ray fluoroscopic imaging apparatus 1;

FIG. 9 is a flowchart illustrating a control operation of a device controller 120 of Embodiment 1 of the X-ray fluoroscopic imaging apparatus 1;

FIG. 10 is a flowchart illustrating the control operation of the device controller 120 of Embodiment 1 of the X-ray fluoroscopic imaging apparatus 1;

FIG. 11 is an explanatory diagram illustrating operations of first and second slide mechanisms of Embodiment 1 of the X-ray fluoroscopic imaging apparatus 1;

FIG. 15 is a flowchart illustrating the control operation of the device controller 120 of Embodiment 3 of the X-ray fluoroscopic imaging apparatus 1;

FIG. 16 is a flowchart illustrating the control operation of the device controller 120 of Embodiment 3 of the X-ray fluoroscopic imaging apparatus 1; and FIG. 17 is an explanatory diagram illustrating the operations of the first and second slide mechanisms of Embodiment 3 of the X-ray fluoroscopic imaging apparatus 1.

DESCRIPTION OF THE PREFERRED EMBODIMENTS

Hereinafter, an embodiment of the present invention will be described with reference to the drawings.

First, an overall configuration of an X-ray fluoroscopic imaging system SY of the present embodiment will be described.

Figure 1:
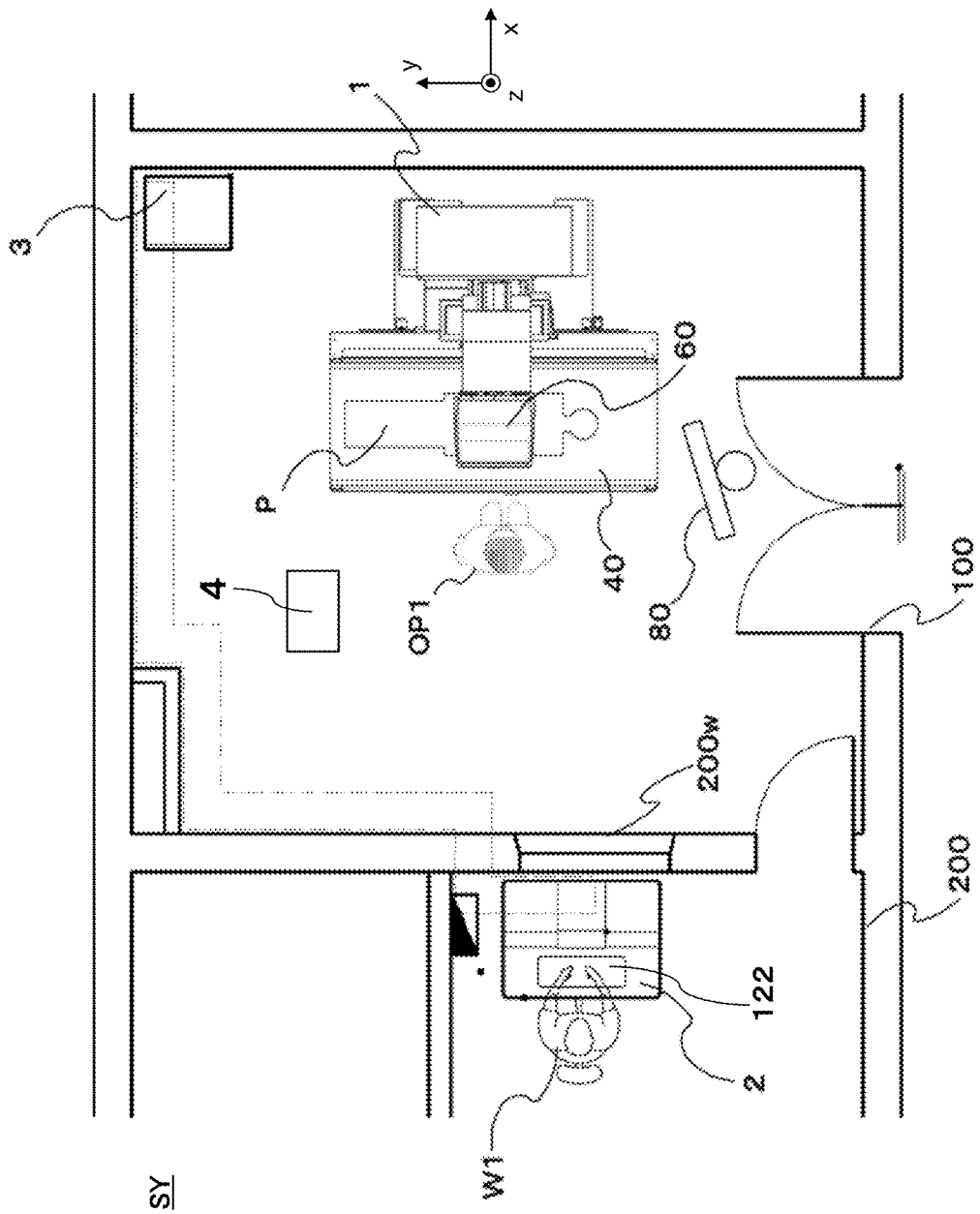
FIG. 1 is a top view illustrating an overall configuration of an X-ray fluoroscopic imaging system SY.

As illustrated in FIG. 1, the X-ray fluoroscopic imaging system SY includes an X-ray fluoroscopic imaging apparatus 1, a high voltage generator 3 for supplying electric power to the imaging apparatus 1, a display device 80 for displaying an image taken, and a remote console 2 and a proximity console 4 for integrally operating these equipments. Among these equipments, the X-ray fluoroscopic imaging apparatus 1, the high voltage generator 3, and the display device 80 are arranged in an imaging room 100 for performing fluoroscopic imaging of a subject P. Further, the remote console 2 includes an operation unit 122 for receiving various operations by a imaging technician W1 such as instructions to a mechanism for operating each part of the X-ray fluoroscopic imaging apparatus 1, and is provided in an operation room 200 adjacent to the imaging room 100. Alternatively, it is also possible to receive an operation by an operator OP1 with the proximity console 4 having the same function in the imaging room 100. When the proximity console 4 receives the operation from the operator OP1, it is preferred that the proximity console 4 includes a mechanism such as a foot pedal that allows the operator OP1 to irradiate X-rays while performing a procedure.

The imaging room 100 has a structure capable of shielding the X-rays generated by the X-ray fluoroscopic imaging apparatus 1 in the room. Therefore, the imaging technician W1 in the operation room 200 is not exposed even if the X-rays are emitted from the X-ray fluoroscopic imaging apparatus 1. Note that a window 200w is provided between the imaging room 100 and the operation room 200, and the imaging technician W1 can monitor a situation inside the imaging room 100 from the operation room 200. The window 200w is made of lead-containing glass or the like so as to shield the X-rays from the imaging room 100.

When performing the procedure such as so-called IVR in which the fluoroscopic imaging of the subject P and a procedure such as catheter insertion are performed in parallel using this imaging system SY, input of X-ray conditions such as X-ray intensity and irradiation interval may be performed with the remote console 2 by the imaging technician W1, or may be performed with the proximity console 4 by the operator OP1. The high voltage generator 3 supplies a tube current having a pulse waveform to the X-ray fluoroscopic imaging apparatus 1 based on the X-ray conditions. The X-ray fluoroscopic imaging apparatus 1 intermittently irradiates the subject P laid on a top plate 40 of the X-ray fluoroscopic imaging apparatus 1 with the X-rays, generates a fluoroscopic image of the subject P by detecting the X-rays transmitted through the subject P, and continuously displays the fluoroscopic image on the display device 80. The operator OP1 stands around the subject P and performs the procedure while looking at the fluoroscopic image displayed on the display device 80.

The operator OP1 changes an X-ray irradiation position on the subject P by operating the mechanism of the X-ray fluoroscopic imaging apparatus 1 described below as necessary while performing the procedure while viewing the fluoroscopic image, and irradiates a field of view of the fluoroscopic image with the X-rays to perform the fluoroscopic imaging.

Embodiment 1

As Embodiment 1, the X-ray fluoroscopic imaging apparatus 1 provided in the above-mentioned X-ray fluoroscopic imaging system SY will be described.

Configuration of Main Part

First, characteristic configuration of the X-ray fluoroscopic imaging apparatus 1 of the present embodiment will be described.

Figure 2:
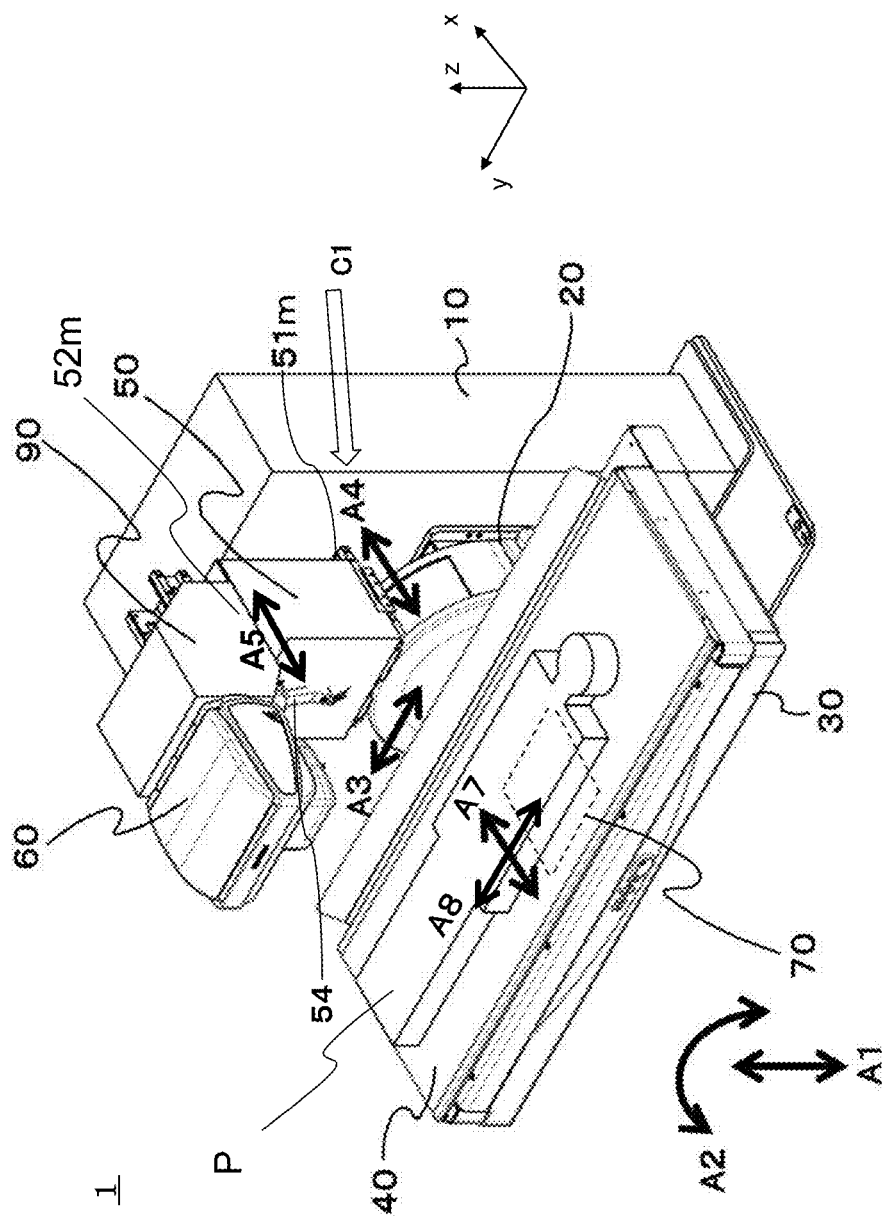
FIG. 2 is a perspective view illustrating a configuration example of an X-ray fluoroscopic imaging apparatus 1.

As illustrated in FIG. 2, the X-ray fluoroscopic imaging apparatus 1 includes a stand 10 mounted on a floor surface, a support column support arm 20 projecting from one side of the stand 10 in a predetermined axial direction (here, an x-axis direction horizontal to the floor surface, and a projecting direction thereof is −x direction), a support column 50 having a lower end mounted on the support column support arm 20, an X-ray support arm 90 mounted on an upper end of the support column 50, and an X-ray generator 60 supported by the X-ray support arm 90. A load of the support column 50 is supported by the support column support arm 20.

A support frame 30 that supports the top plate 40 on which the subject P is mounted is also supported on the support column support arm 20. A long axis direction of the top plate 40 is parallel to a y direction. The support column 50 is mounted on the support column support arm 20 between the stand 10 and the support frame 30. An X-ray detector 70 is disposed in the support frame 30.

The X-ray generator 60 is supported above the top plate 40 by the support column 50 and the X-ray support arm 90. The X-ray generator 60 irradiates the subject P mounted on the top plate 40 with the X-rays, and the X-rays transmitted through the subject P are detected by the X-ray detector 70.

Figure 3:
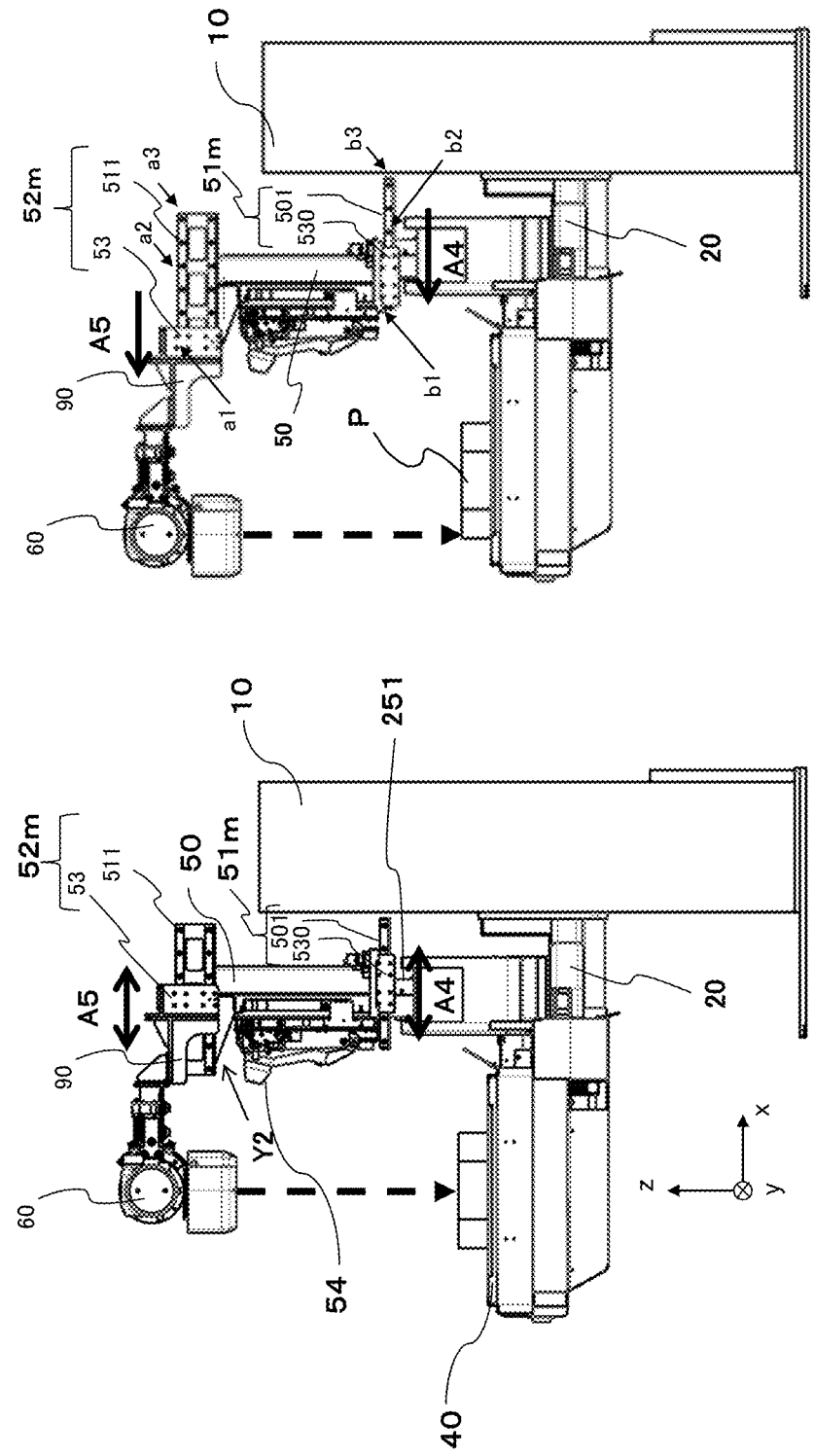
FIGS. 3A and 3B are partial side views illustrating an operation example of the X-ray fluoroscopic imaging apparatus 1.

As illustrated in FIG. 3A, a first slide mechanism 51m for sliding a lower end of the support column 50 in a direction of an arrow A4 parallel to the x-axis direction with respect to the support column support arm 20 is disposed between the support column support arm 20 and the lower end of the support column 50. Further, a second slide mechanism 52m for sliding the X-ray support arm 90 in a direction of an arrow A5 parallel to a predetermined direction with respect to the upper end of the support column 50 is disposed between the upper end of the support column 50 and the X-ray support arm 90.

By respectively arranging the first slide mechanism 51m and the second slide mechanism 52m at the lower end and the upper end of the support column 50 in this way, not only the X-ray support arm 90 to which the X-ray generator 60 is connected but also an entire support column 50 can be slid parallel to the x-axis direction. Therefore, the X-ray fluoroscopic imaging apparatus 1 of the present embodiment can be moved in a wide range in the x-axis direction of the X-ray generator 60.

Figure 4:
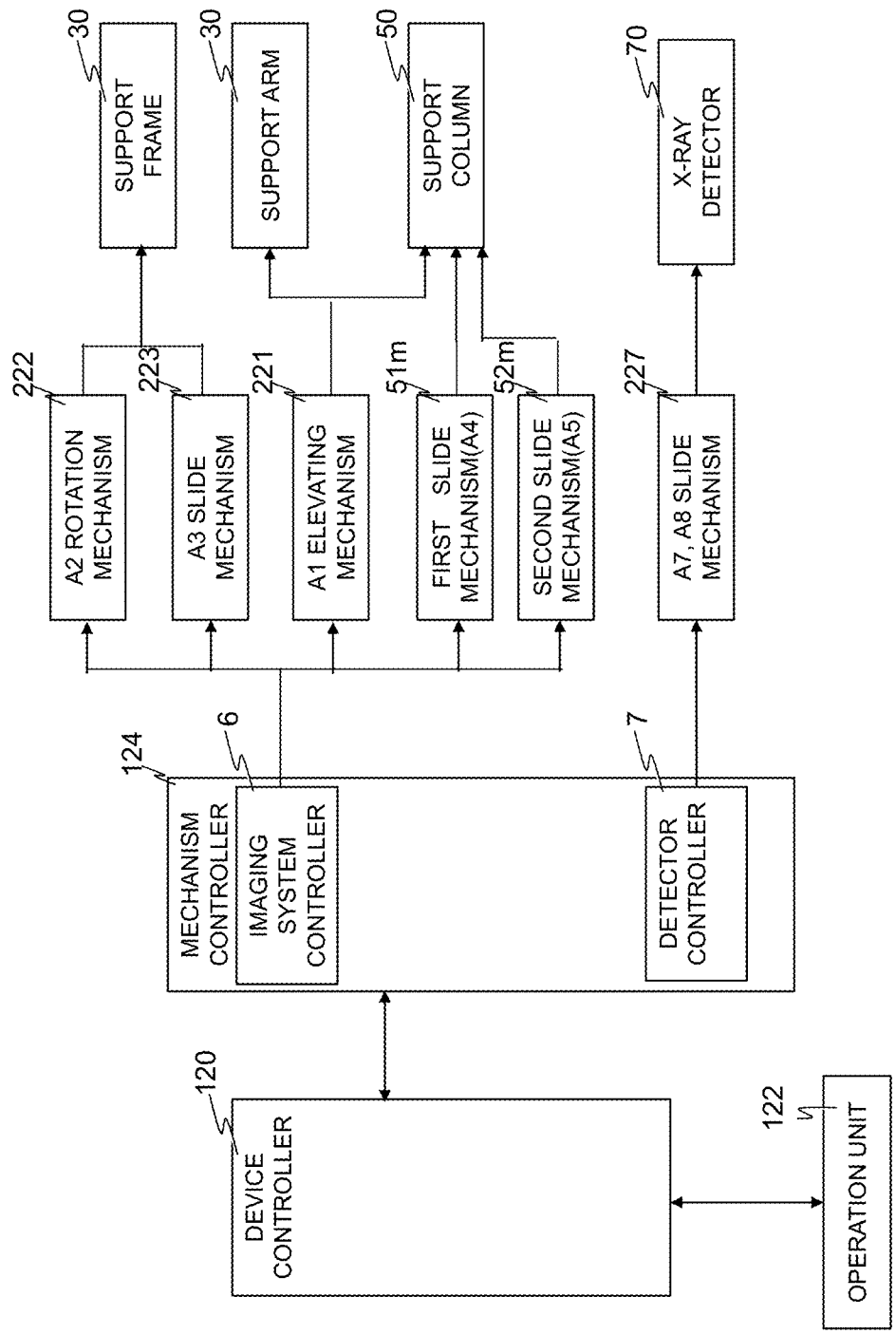
FIG. 4 is a block diagram illustrating the configuration example of the X-ray fluoroscopic imaging apparatus 1.

As illustrated in FIG. 4, a device controller 120 is connected to the first and second slide mechanisms 51 via a mechanism controller 124, and the device controller 120 controls operations of the mechanisms.

The operation unit 122 for receiving an instruction from a user to move the X-ray generator 60 at least in the x-axis direction is connected to the device controller 120.

In the present embodiment, when the operation unit 122 has received the instruction from the user to move the X-ray generator 60 in the x-axis direction (for example, −x direction), the device controller 120 performs the following first mode and second mode in order.

In the first mode, as illustrated in FIG. 3B, the device controller 120 operates the second slide mechanism 52m to move the X-ray support arm 90 in the x-axis direction with respect to the upper end of the support column 50.

Next, in the second mode, the device controller 120 operates the first slide mechanism 51m to move the lower end of the support column 50 at a predetermined first speed in a direction (here, −x direction) instructed by the user with respect to the support column support arm 20, while operating the second slide mechanism 52m to move the X-ray support arm 90 at a second speed smaller than the first speed in a direction (+x direction) opposite to the direction (−x direction) instructed by the user with respect to the upper end of the support column 50. Thus, the X-ray generator 60 moves in the direction (here, −x direction) instructed by the user at a speed of a difference between the first speed and the second speed.

In this way, in the first mode, since the second slide mechanism 52m is first operated to start moving the X-ray generator 60 to move only the X-ray support arm 90 that supports the X-ray generator 60, a weight of a structure to be moved can be reduced as compared with a case where the first slide mechanism 51m moves the X-ray support arm 90 together with the support column 50 that supports the X-ray support arm 90. Therefore, movement of the X-ray generator 60 can be started quickly and smoothly.

After moving the X-ray generator 60 in the first mode, the support column 50 is moved by the first slide mechanism 51m in the second mode, so that the X-ray generator 60 can be moved to a range that cannot be reached only by sliding of the second slide mechanism 52m.

In the second mode, while the support column 50 is moved, the X-ray support arm 90 is moved in a direction opposite to a movement direction of the support column 50 at a speed smaller than a movement speed of the support column 50. Thus, the X-ray support arm 90 that has moved near an end of a slide movable range of the second slide mechanism 52m in the first mode can be returned to a central portion of the slide movable range.

Thus, after the support column 50 has moved to an end of a movable range of the first slide mechanism 51m, the X-ray generator 60 can be moved by sliding the X-ray support arm 90 by the second slide mechanism 52m. Therefore, when the X-ray generator 60 reaches a desired position, the movement of the X-ray generator 60 is stopped by stopping an operation of the second slide mechanism 52m that slides the X-ray support arm 90. That is, by stopping movement of the X-ray support arm 90, which is lighter than a case of stopping movement of the support column 50, a response to a stop instruction is good and an inertial force is small, so that the movement of the X-ray generator 60 can be stopped smoothly without generating vibration or the like.

A change from the first mode to the second mode can be performed at a desired timing. For example, the device controller 120 can be configured to perform the second mode when the X-ray generator 60 reaches a predetermined position in the movable range of the second slide mechanism 52m in the first mode. Further, when the operation unit 122 has a structure (for example, a joystick) having a function of receiving instructions of low-speed movement and high-speed movement from the user, the device controller 120 can be configured to first perform the first mode when it receives the low-speed movement, and switch from performing the first mode to performing the second mode when the operation unit 122 is switched from the low-speed movement to the high-speed movement.

Detailed Configuration

The configuration of the X-ray fluoroscopic imaging apparatus 1 will be described in more detail.

Specific configurations of the first slide mechanism 51m and the second slide mechanism 52m will be described below.

A drive mechanism, which raises and lowers and rotates the support frame 30 of the top plate 40 and the support column support arm 20 for supporting the support column 50 that supports the X-ray generator 60, is disposed inside the stand 10. Specifically, the stand 10 incorporates an elevating mechanism 221 (hereinafter referred to as an A1 elevating mechanism) that allows the support column support arm 20 to be raised and lowered in a direction of an arrow A1 of FIG. 2, and a rotation mechanism 222 (hereinafter referred to as an A2 rotation mechanism) that rotates the support column support arm 20 about a central axis thereof as shown by an arrow A2 (see FIG. 4).

The mechanism 221 allows the support frame 30 to be raised and lowered while maintaining a distance between the X-ray generator 60 and the X-ray detector 70, that is, a distance (SID) between an X-ray tube focus and an image receiving surface. Further, by raising and lowering the support frame 30, a height of the top plate 40 can be adjusted to a position where the subject P can be easily placed on the top plate 40 or the operator can easily perform operations.

The stand 10 has the rotation mechanism 222 that can rotate the support column support arm 20 about an axis parallel to a short axis direction of the top plate 40 (see FIG. 4). A rotatable range of the support frame 30 by the mechanism 222 is preferably about ±90° from a horizontal state with respect to the floor surface, and about 180° in total. Since the support column support arm 20 has such a rotatable structure, a posture of the subject P on the top plate 40 can be set at an arbitrary angle between a standing state and a lying state.

The support column support arm 20 is provided with a slide mechanism 223 (hereinafter referred to as an A3 slide mechanism) that allows the support column 50 to move in the long axis direction (A3 direction; y direction in FIG. 2) of the top plate 40 with respect to the support column support arm 20 (see FIG. 4).

The support frame 30 further incorporates a detector moving mechanism (hereinafter referred to as a detector slide mechanism) 227 (see FIG. 4) that slides the X-ray detector 70 in the short axis direction (an arrow A7 direction) and the long axis direction (an arrow A8 direction) of the top plate 40.

Since known structures can be used for the mechanisms 221 to 223 and 227, detailed description of the mechanisms will be omitted.

Figure 5:
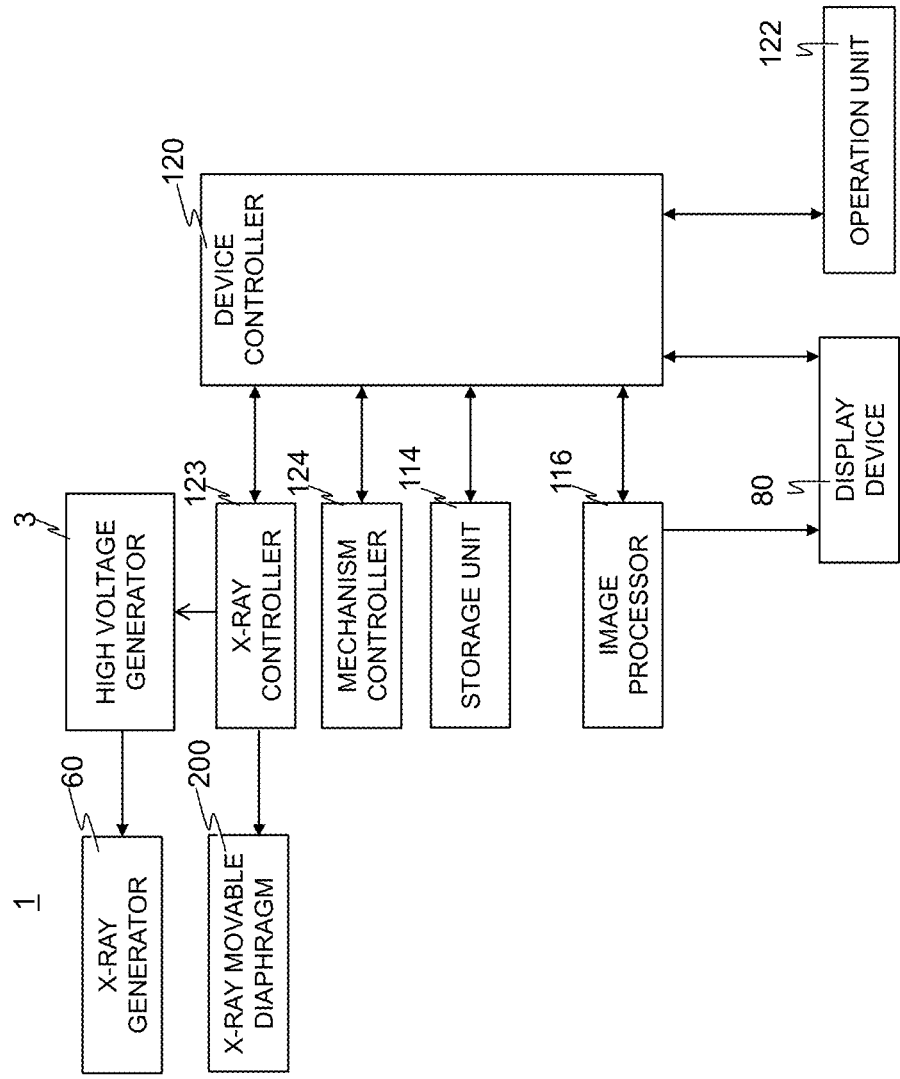
FIG. 5 is a block diagram illustrating a configuration example of a control system of each mechanism of the X-ray fluoroscopic imaging apparatus 1.

The X-ray generator 60 incorporates the X-ray tube, and as illustrated in FIG. 5, receives power from the high voltage generator 3 through a cable (not shown) to generate the X-rays from the X-ray tube. The X-ray generator 60 may include an X-ray movable diaphragm 200 that limits the X-ray irradiation range, an X-ray filter that selectively transmits the X-rays of a specific energy, or the like.

As the X-ray detector 70, a combination of an image intensifier and a TV camera, an X-ray flat panel detector (FPD), or the like can be used. In particular, considering that the X-ray detector is disposed in the support frame, it is preferable to use a small and lightweight FPD. The X-ray detector 70 is disposed inside the support frame 30 so as to face the X-ray generator 60, and detects the X-rays that have passed through the subject P. In the present embodiment, the slide mechanism 227 moves the X-ray detector 70 in the short axis (A7) direction and the long axis (A8) direction of the top plate in conjunction with a position of the X-ray generator 60 so that an optical axis of the X-rays emitted from the X-ray generator 60 always penetrates a center of the X-ray detector 70.

Configuration of Control System

As illustrated in FIG. 5, the X-ray fluoroscopic imaging apparatus 1 includes an image processor 116 that performs image processing on an X-ray signal output from the X-ray detector 70, a storage unit 114 that stores various information such as X-ray images processed by the image processor 116, and the device controller 120 that integrates and controls components. The X-ray image processed by the image processor 116 is displayed on the display device 80 via the device controller 120.

Functions of the device controller 120 are implemented by software loaded on a CPU or a GPU. Further, some or all the functions of the device controller 120 can also be realized by hardware such as an ASIC (Application Specific Integrated Circuit) or an FPGA (Field Programmable Gate Array).

The X-ray fluoroscopic imaging apparatus 1 includes an X-ray controller 123 and the mechanism controller 124 for controlling the operation of each part together with the device controller 120 described above.

The X-ray controller 123 controls the X-ray generator 60 and the X-ray movable diaphragm 200 to adjust a dose of the X-rays emitted from the X-ray generator 60.

The mechanism controller 124 controls a mechanism for moving each part of the apparatus. As illustrated in FIG. 4, the mechanism controller 124 has an imaging system controller that adjusts the X-ray irradiation position (imaging position) and a detector controller 7 that adjusts a position of the X-ray detector 70 depending on the imaging position.

Further, the device controller 120 is connected to the operation unit 122, and when it receives operation information by the imaging technician W1 received by the operation unit 122, it transmits the instruction to the mechanism controller 124 and the like based on the information.

The above-mentioned mechanisms, that is, the A1 elevating mechanism 221 and the A2 rotation mechanism 222, the A3 slide mechanism 223, the first slide mechanism 51$m$ (A4), and the second slide mechanism 52$m$ (A5) are connected to the imaging system controller 6. The imaging system controller controls operations of the mechanisms according to instruction information for operating each unit received by the operation unit 122, to adjust the imaging position. Further, the detector slide mechanism 227 is connected to the detector controller 7 and adjusts the position of the X-ray detector 70 in conjunction with the position of the X-ray generator 60.

The operation unit 122 may be provided with a lever (for example, the joystick) or a button that receives movement conditions of the apparatus, or may have a UI such as a keyboard or a touch panel that receives the movement conditions by numerical input or the like. The imaging technician W1 can control the operation of the X-ray fluoroscopic imaging apparatus 1 in directions of the arrows A1 to A5, A7 and A8 under the control of the detector controller 7 by inputting the movement conditions such as a movement direction and a movement amount via the operation unit 122. Note that the controllers described above may be partially or wholly provided in the imaging room 100.

Configuration of First and Second Slide Mechanisms 51$m$ and 52$m$

Figure 6:
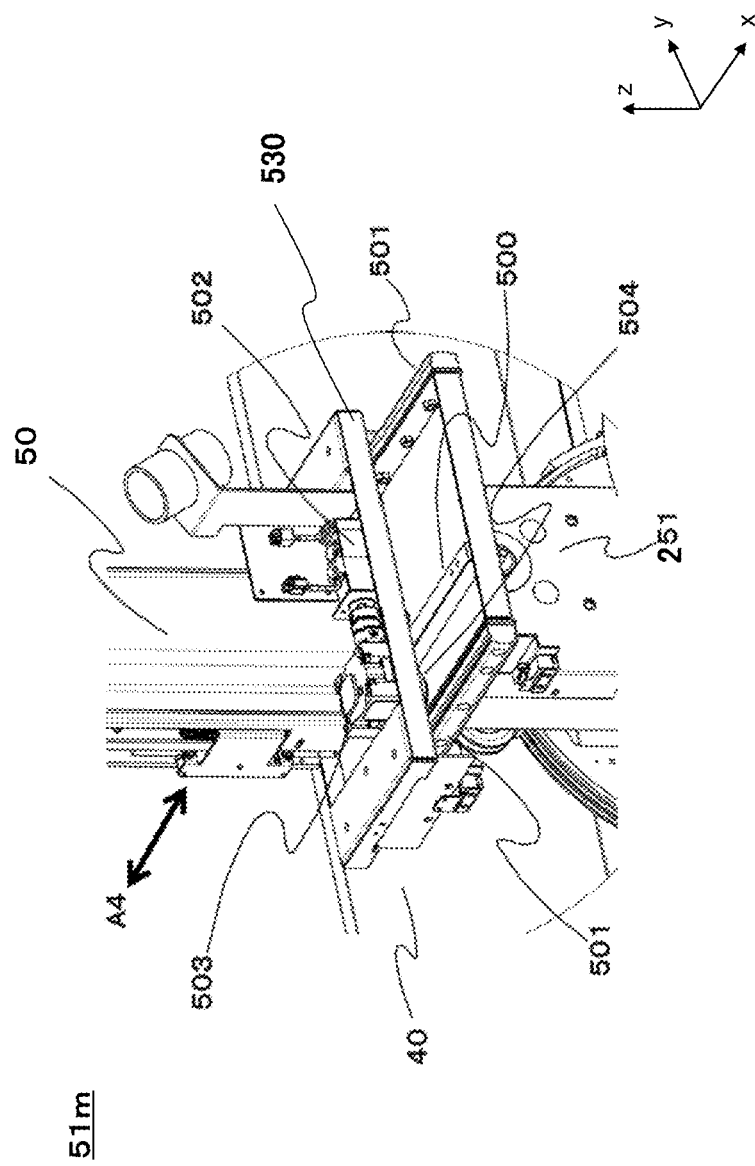
FIG. 6 is a partial perspective view illustrating a configuration of a slide mechanism 51m.

Next, specific configurations of the support column 50 and the first slide mechanism 51$m$ will be described with reference to FIGS. 3A, 3B and 6. FIGS. 3A, 3B and 6 illustrate a state in which an exterior of the apparatus is removed for the sake of explanation. Note that FIG. 6 is a perspective view of the first slide mechanism 51$m$ from a direction of an arrow C1 (that is, viewed from the stand 10 side) with the exterior in FIG. 2 removed.

A base portion 251 for supporting the first slide mechanism 51$m$ is fixed on the support column support arm 20. The first slide mechanism 51$m$ includes two support column guide rails 501 fixed to an upper end of the base portion 251 and a rectangular plate-shaped support column slide portion 530 fixed to a lower end of the support column 50. A long axis direction of the support column guide rail 501 is parallel to the x-axis direction. The support column slide portion 530 engages with the support column guide rails 501 and can move on the support column guide rails 501 in the +x and −x directions.

A rack 500 is disposed in parallel with the support column guide rails 501 between the two support column guide rails 501. On the other hand, a pinion 504 that meshes with the rack 500 is disposed on a bottom surface of the support column slide portion 530. The support column slide portion 530 is equipped with a motor 502 for rotating the pinion 504 and a reduction gear 503 for transmitting rotation of the motor 502 to the pinion 504.

The operation of the motor 502 is controlled by the device controller 120 via the mechanism controller 124. Thus, the device controller 120 instructs the motor 502 to rotate via the mechanism controller 124, and the pinion 504 rotates with the rotation of the motor 502, so that the pinion 504 moves along the support column guide rails 501. Thus, the support column slide portion 530 on which the support column 50 is mounted can be moved in the x-axis direction along the support column guide rails 501. Further, by changing a rotation direction of the motor 502, the movement direction of the support column 50 can be switched to the −x direction or the +x direction.

Note that a compression tube 54 that compresses a region of interest of the subject P during imaging is disposed on a side surface of the support column 50.

Next, the configuration of the second slide mechanism 52m will be described with reference to FIG. 7.

The second slide mechanism 52m includes two guide rails 511 fixed to the upper end of the support column 50, and an X-ray slide portion 53 fixed to an end of the X-ray support arm 90 on the stand 10 side. A long axis direction of the guide rail 511 is parallel to the x-axis direction. The X-ray slide portion 53 engages with the guide rails 511 and can move on the guide rails 511 in the +x direction and the −x direction.

A rack 510 is disposed in parallel with the guide rails 511 between the two guide rails 511. On the other hand, a pinion 513 that meshes with the rack 510 is disposed inside the X-ray slide portion 53. A motor 512 for rotating the pinion 513 is mounted on the X-ray slide portion 53.

The operation of the motor 512 is controlled by the device controller 120 via the mechanism controller 124. Thus, the device controller 120 instructs the motor 512 to rotate via the mechanism controller 124, and the pinion 513 rotates with rotation of the motor 512, so that the pinion 513 moves along the rack 510. Thus, the X-ray slide portion 53 fixed to the X-ray support arm 90 can be moved in the x-axis direction along the guide rails 511. Further, by changing a rotation direction of the motor 512, the movement direction of the support column 50 can be switched to the −x direction or the +x direction.

In the X-ray fluoroscopic imaging apparatus 1, the movable range of the first slide mechanism 51m can be designed to be, for example, 200 mm, and the movable range of the second slide mechanism 52m can be designed to be, for example, 400 mm. Thus, the X-ray generator 60 can move 600 mm. Thus, the X-ray irradiation range (that is, an imaging range) can be moved from one end to the other end in the short axis direction of the top plate 40.

Operation

Hereinafter, an operation example of the fluoroscopic imaging and X-ray imaging of the X-ray fluoroscopic imaging apparatus 1 will be described with reference to FIG. 8 and the like.

Step s1

The imaging technician W1 operates the operation unit 122 to operate the A1 elevating mechanism 221 so that the subject P can easily ride on the top plate 40, to adjust a height of the support frame 30. At this point, as illustrated in FIG. 3A, a support column body 52 is in a state of being stored closest to the stand 10.

Step s2

In this state, the operator OP1 lays the subject P on the top plate 40.

Step s3

The device controller 120 determines whether the operation unit 122 has been operated by the imaging technician W1 to receive an operation of moving the imaging position, and if the operation unit 122 has received the operation of moving the imaging position, it proceeds to Step s4, and if the operation unit 122 has not received the operation of moving the imaging position, it proceeds to Step s5.

Step s4

The imaging system controller 6 controls the operation of each mechanism depending on the imaging position input by the imaging technician W1, and moves the X-ray generator 60 in the long axis direction and the short axis direction of the top plate 40, to place it at a start position of the fluoroscopic imaging. When changing inclination of the support frame 30, the distance (SID) between the X-ray generator 60 and the X-ray detector 70 is maintained.

Step s5

The device controller 120 determines whether the operation unit 122 has received the instruction to start fluoroscopic imaging from the imaging technician W1, and if the operation unit 122 has received the instruction for fluoroscopic imaging, it proceeds to Step s6, and if not, the process returns to Step s3.

Step s6

The X-rays are emitted from the X-ray generator 60 at predetermined intervals, and the fluoroscopic imaging is started. The captured fluoroscopic image is displayed on the display device 80, and the operator performs the procedure on the subject P while looking at the fluoroscopic image displayed on the display device 80.

Step s7

The device controller 120 determines whether the operation unit 122 has received the instruction to move the imaging position in the x-axis direction (short axis direction of the top plate 40) by the imaging technician W1, and if the operation unit 122 has received the instruction, it proceeds to Step s8, and if not, it proceeds to Step s9.

Step s8

The imaging system controller 6 drives the first and second slide mechanisms 51m and 52m as illustrated in FIG. 3B in a state where the fluoroscopic imaging is continued, and moves the X-ray generator 60 to the subject P side (arrow A4) in the short axis direction of the top plate 40. Specifically, the imaging system controller 6 operates the first and second slide mechanisms 51m and 52m in response to the instruction received by the device controller 120, to move the X-ray generator 60.

At the same time, the detector slide mechanism 227 moves the position of the X-ray detector 70 in conjunction with the first and second slide mechanisms 51m and 52m, so that the optical axis of the emitted X-rays always penetrates the center of the X-ray detector 70.

Step s9

The device controller 120 determines whether the operation unit 122 has received an X-ray imaging instruction from the imaging technician W1, and if the operation unit 122 has received the instruction, it proceeds to Step s10, and if not, it proceeds to Step s11.

Step s10

The imaging system controller 6 increases a rotation speed of an anode of the X-ray tube of the X-ray generator 60 and supplies a predetermined tube current and tube voltage from the high voltage generator 3 to the X-ray tube, to emit the X-rays having a larger energy than during fluoroscopy. At this time, the movement of the X-ray generator 60 by the first and second slide mechanisms 51m and 52m is temporarily stopped at the timing of increasing the rotation speed of the anode. Thus, it is possible to irradiate the X-rays and take the X-ray image while the X-ray generator 60 is positioned. The X-ray image is displayed on the display device 80. When the X-ray imaging is completed, the movement of the X-ray generator 60 and the X-ray detector 70, and the fluoroscopic imaging are resumed.

Step s11

The device controller 120 determines whether the operation unit 122 has taken the fluoroscopic image up to a predetermined position received from the imaging technician W1, and if the predetermined position is reached, it proceeds to Step s12, and if not, it returns to Step s6.

Step s12

Since the fluoroscopic imaging has reached the predetermined position, the fluoroscopic imaging ends. Specifically, the device controller 120 stops the X-ray irradiation by the X-ray generator 60 and stops the operations of the first and second slide mechanisms 51m and 52m.

Step S13

The imaging system controller 6 adjusts the height of the support frame 30 so that the subject P can easily get off the top plate 40.

In this way, the fluoroscopic imaging of the subject is performed by the X-ray fluoroscopic imaging apparatus 1 of Embodiment 1.

Movement of X-Ray Generator 60 in x-Axis Direction

Next, a control operation of the device controller 120 when the X-ray generator 60 moves in the x-axis direction in Step s8 will be described in more detail with reference to a flow of FIGS. 9 and 10 and FIG. 11.

FIG. 11 is a diagram schematically illustrating a positional relationship between the support column guide rail 501 fixed to the support column support arm 20 and the support column slide portion 530 that slides on the support column guide rails 501 together with the support column 50, and a positional relationship between the X-ray guide rail 511 fixed to the upper end of the support column 50 and the X-ray slide portion 53 that slides on the X-ray guide rails 511 together with the X-ray generator 60 and the X-ray support arm 90. In FIG. 11, a height or the like of the support column 50 is different from an actual size. Note that "I-00" in FIG. 11 is an initial state. An end of the X-ray guide rail 511 on the stand 10 side is a3, a center position thereof is a2, and an end thereof farthest from the stand 10 is a1. Further, an end of the support column guide rail 501 on the stand 10 side is b3, a center position thereof is b2, and an end thereof farthest from the stand 10 is b1. It will be described below assuming that the support column guide rail 501 and the X-ray guide rail 511 have the same length here and a total length thereof is a movable range of the support column slide portion 530 and the X-ray slide portion 53.

In the initial state (I-00) in which the first and second slide mechanisms 51m and 52m are not operated, the X-ray slide portion (hereinafter, also referred to as an A5 axis connection point) 53 of the second slide mechanism 52m is located at the center position a2 of the guide rail 511. The support column slide portion 530 is located at the center position b2 of the support column guide rail 501. In the initial state (I-00), the guide rail 511 is directly above the support column guide rail 501, that is, the positions a1, a2, and a3 are respectively at the same positions with (corresponding positions to) the positions b1, b2, and b3 in the x-axis direction.

In Step s7 of FIG. 8, when the operation unit 122 has received the instruction to move the imaging position in the x-axis direction by the imaging technician W1, the device controller 120 proceeds to Step s8 and performs the flow of FIGS. 9 and 10.

Step 131

First, the device controller 120 determines whether the movement direction received in Step s7 is a plus direction (+x direction: direction approaching the stand 10) or a minus direction (−x direction: direction away from the stand 10) of the x-axis. If the received movement direction is the −x direction, it proceeds to Step 132. If the received movement direction is in the +x direction, it proceeds to Step 142 in FIG. 10.

Step 132

In Step 132, the device controller 120 operates the motor 512 of the second slide mechanism 52m to move the X-ray slide portion (A5 axis connection point) 53 in the −x direction with respect to the guide rail 511 (first mode). Thus, the X-ray generator 60 and the X-ray support arm 90 move in the −x direction with respect to the upper end of the support column 50 (movement from I-00 to I-11 in FIG. 11).

As described above, in Step 132, in order to move the X-ray generator 60, only the X-ray support arm 90 and the X-ray generator 60 supported by the support column 50 are moved, and the support column 50 is not moved, so that a weight of a part to be moved can be suppressed, and the movement can be started smoothly with a quick reaction.

Step 133

The device controller 120 determines whether the X-ray slide portion (A5 axis connection point) 53 has reached a predetermined position R1 (I-11 in FIG. 11) between the positions a1 and a2 of the guide rail 511 based on a drive amount of the motor 512, and if the X-ray slide portion 53 has reached the predetermined position, it proceeds to Step 134. If the X-ray slide portion 53 has not reached the predetermined position, it returns to Step 132 to continue the movement.

Step 134

In Step 134, the device controller 120 operates the first slide mechanism 51m to move the support column slide portion 530 on which the support column 50 is mounted in the −x direction at a first speed v1, while moving the X-ray slide portion (A5 axis connection point) 53 at a second speed v2 in the +x direction opposite to the −x direction in which the operation unit 122 has received the movement instruction (I-12 in FIG. 11). Note that the device controller 120 sets the first speed v1 to be larger than the second speed v2 (second mode).

By these operations, the X-ray generator 60 advances in the −x direction at a speed of a difference between the first speed v1 and the second speed v2, and the X-ray slide portion (A5 axis connection point) 53 returns on the guide rail 511 in the +x direction, so that a position of the X-ray slide portion (A5 axis connection point) 53 on the guide rail 511 approaches the center position a2. Therefore, after that, the X-ray slide portion (A5 axis connection point) 53 can be moved on the guide rail 511 regardless of whether the direction of the movement instruction received by the operation unit 122 is the −x direction or the +x direction, and the X-ray generator 60 can be moved quickly and smoothly.

Step 135

In Step 135, the device controller 120 determines whether the X-ray slide portion (A5 axis connection point) 53 has reached the center position a2 of the guide rail 511, and the center position a2 of the guide rail 511 has reached the end b1 of the support column guide rail 501 (positional relationship (a2, (a2, b1)) shown by I-12 in FIG. 11), and if so, it proceeds to Step 136.

Step 136

In Step 136, the device controller 120 moves the X-ray slide portion (A5 axis connection point) 53 in the −x direction on the guide rail 511 (I-13 in FIG. 11).

Step 137

Then, the device controller 120 determines whether the X-ray slide portion (A5 axis connection point) 53 has reached the predetermined position R1 between the positions a1 and a2 of the guide rail 511, and if the X-ray slide portion has reached the position R1, it proceeds to Step 138. If the X-ray slide portion has not reached the position R1, it returns to Step 136 and moves the X-ray slide portion further.

Step 138

In Step 138, as in Step 134, the device controller 120 operates the first slide mechanism 51m to move the support column slide portion 530 on which the support column 50 is mounted in the −x direction at the first speed v1, while moving the X-ray slide portion (A5 axis connection point) 53 at the second speed v2 with respect to the guide rail 511 in the +x direction opposite to the −x direction in which the operation unit 122 has received the movement instruction (I-14 in FIG. 11) (v1>v2, second mode).

Thus, the X-ray generator 60 further advances in the −x direction at the speed of the difference (v1−v2) between the first speed v1 and the second speed v2, and the X-ray slide portion (A5 axis connection point) 53 returns on the guide rail 511 in the +x direction and approaches the center position a2.

Step 139

In Step 139, the device controller 120 determines whether the X-ray slide portion (A5 axis connection point) 53 has reached the center position a2 of the X-ray guide rail 511, and the center position a2 of the X-ray guide rail 511 has reached the end b1 of the support column guide rail 501 (position represented by a positional relationship (a2, (a3, b1)) shown by I-12 in FIG. 11), and if so, it proceeds to Step 140.

Step 140

In Step 140, as in Step 132, the device controller 120 moves the X-ray slide portion (A5 axis connection point) 53 in the −x direction with respect to the X-ray guide rail 511. Thus, the X-ray generator 60 moves in the −x direction with respect to the upper end of the support column 50 (movement from I-14 to I-15 in FIG. 11).

Step 141

The device controller 120 determines whether the X-ray slide portion (A5 axis connection point) 53 reaches the end a1 of the X-ray guide rail 511, and the end a3 of the X-ray guide rail 511 on the stand 10 side has reached a position in which it overlaps the end b1 of the support column guide rail 501 of the first slide mechanism 51m (see I-15 in FIG. 11: (a1, (a3, b1))), and if so, it stops the movement and ends.

Steps 142 to 151

In Step 131 described above, when the movement direction received by the operation unit 122 is the +x direction, Steps 142 to 151 are performed to move the X-ray detector 60 in the +x direction.

Since the operations of Steps 142 to 151 correspond to the operations of Steps 132 to 141 described above except that the movement direction is reversed, and the reaching position R1 of the X-ray slide portion (A5 axis connection point) 53, which is the timing for switching from the first mode to the second mode, is R2, detailed description thereof will be omitted.

As described above, in the present embodiment, the slide mechanisms 51m and 52m are respectively provided on an upper portion and a lower portion of the support column 50, and the X-ray generator 60 can be moved within a large movable range by not only moving the X-ray generator 60 but also moving the support column 50 together, however, since the first mode and the second mode are performed in order, when the movement of the X-ray generator 60 is started and stopped, the movement of the X-ray slide portion (A5 axis connection point) 53 of the slide mechanism 52m on the upper portion is started and stopped. Therefore, the movement of the X-ray generator 60 can be started and stopped smoothly with a quick reaction as compared with the case where the movement of the heavy support column 50 is started and stopped by the slide mechanism 51m on the lower portion of the support column 50.

When a fluoroscopic imaging instruction is given in an imaging switch in which the user instructs to perform the fluoroscopic imaging and the X-ray imaging, the device controller 120 generates the X-rays from the X-ray generator while performing the first mode and the second mode. On the other hand, when the imaging switch receives an X-ray imaging instruction, the first mode and the second mode may be stopped to be performed, to expose the X-rays from the X-ray generator 60.

Embodiment 2

In Embodiment 2, the device controller 120 performs a third mode in which the support column slide portion 530 on which the support column 50 is mounted and the X-ray slide portion (A5 axis connection point) 53 on which the X-ray support arm 90 is mounted are moved as in the second mode, even after the movement instruction from the user is stopped after the first mode or the second mode, and prepares for the next movement instruction to be received. That is, in the third mode, while the support column slide portion 530 is moved in the direction instructed to move by the user in the previous mode, the X-ray slide portion (A5 axis connection point) 53 is moved in the opposite direction, and the position of the X-ray generator 60 is maintained unchanged by making both movement speeds equal. Thus, when the movement instruction is received from the user in the next step, a distance at which the X-ray support arm 90 can be moved with respect to the support column 50 can be increased.

Hereinafter, the control operation of the device controller 120 of Embodiment 2 will be specifically described with reference to a flow of FIGS. 12 and 13 and FIG. 14.

Figure 14:
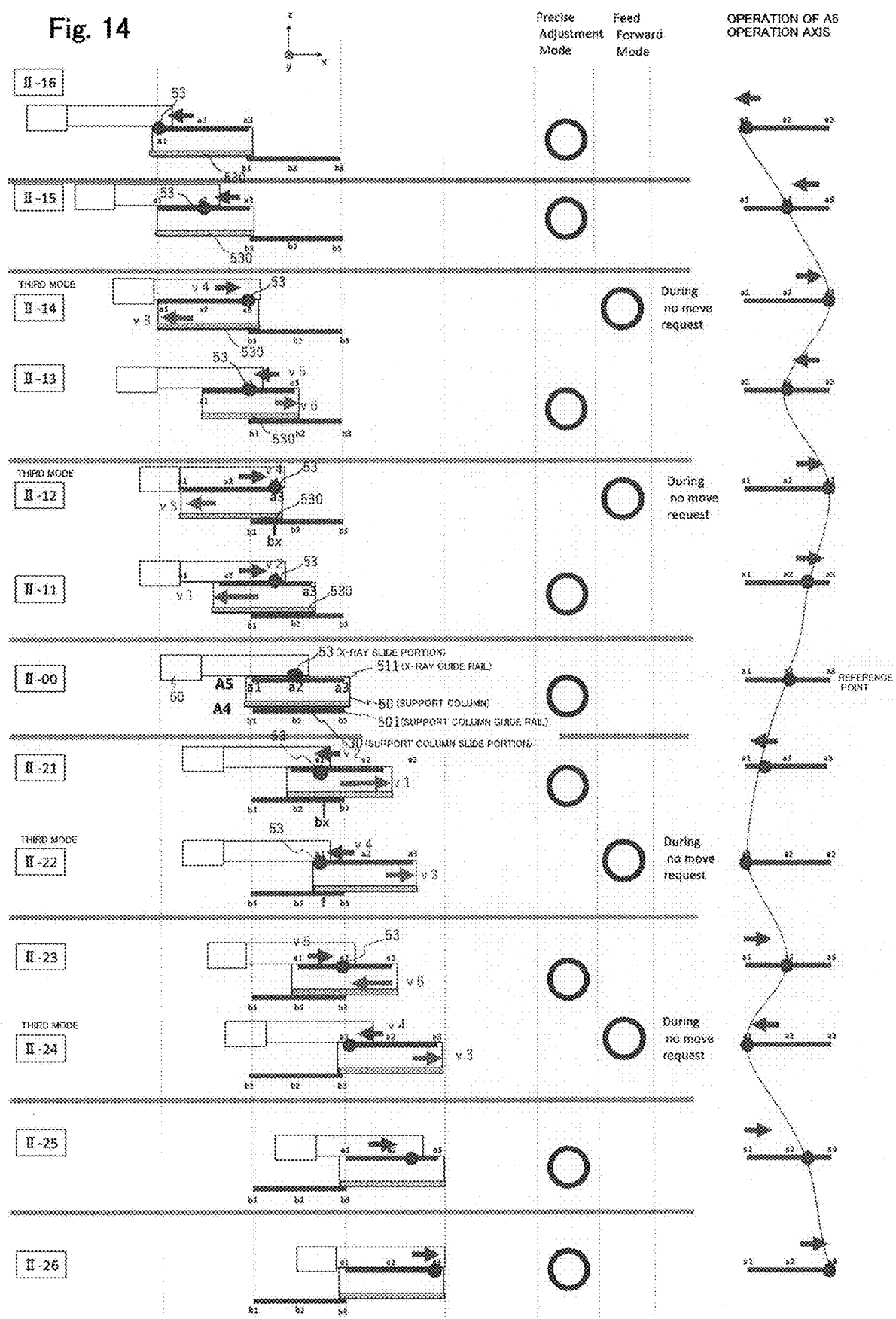
FIG. 14 is an explanatory diagram illustrating the operations of the first and second slide mechanisms of Embodiment 2 of the X-ray fluoroscopic imaging apparatus 1.

As in FIG. 11, FIG. 14 is a diagram schematically illustrating the positional relationship between the support column guide rail 501 fixed to the support column support arm 20 and the support column slide portion 530 equipped with the support column 50 and sliding on the support column guide rails 501, and a positional relationship between the X-ray guide rail 511 fixed to the upper end of the support column 50 and the X-ray slide portion 53 that slides on the X-ray guide rails 511 together with the X-ray generator 60 and the X-ray support arm 90. "II-00" in FIG. 14 is the initial state like "I-00" in FIG. 11.

Figure 12:
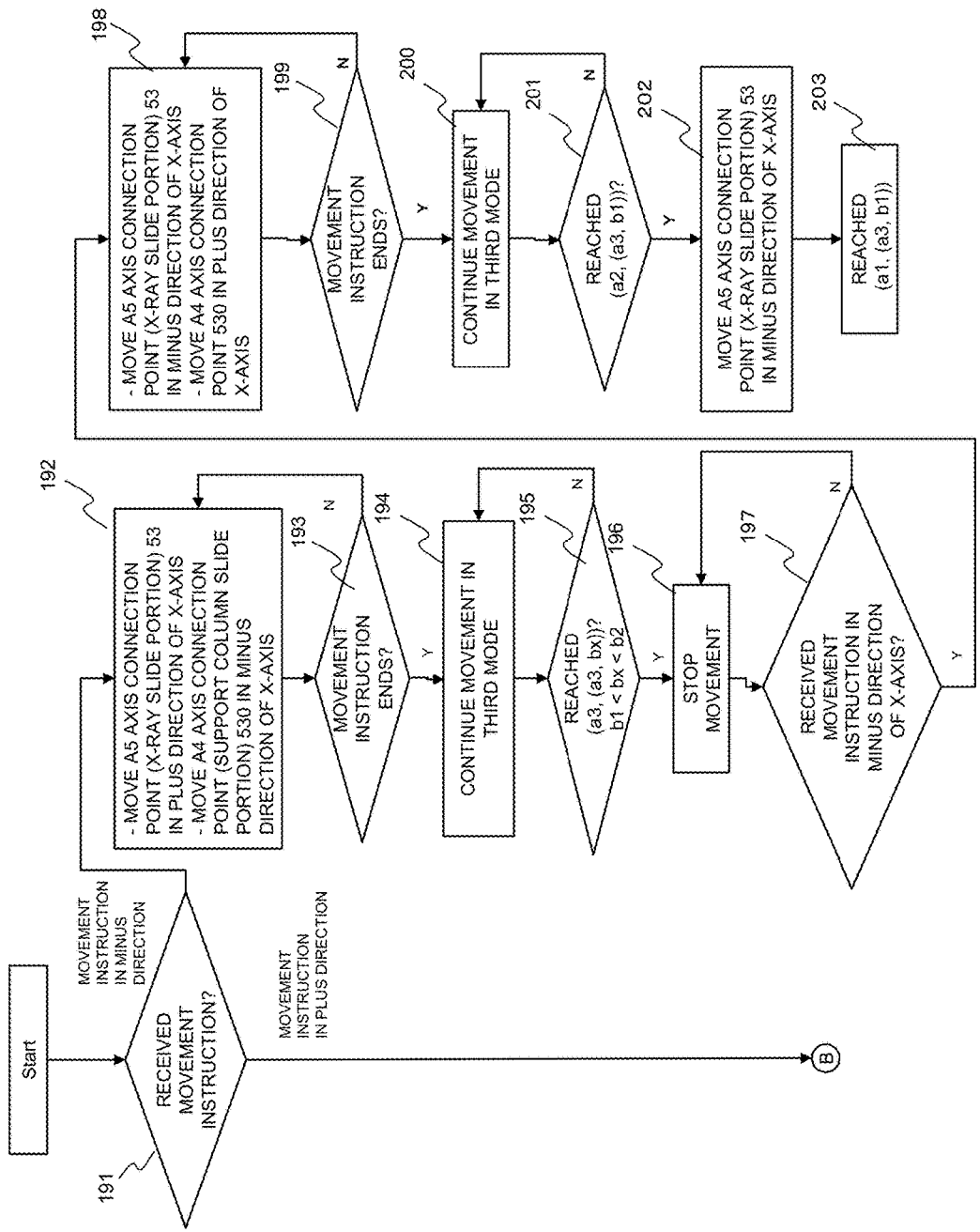
FIG. 12 is a flowchart illustrating the control operation of the device controller 120 of Embodiment 2 of the X-ray fluoroscopic imaging apparatus 1.
Figure 13:
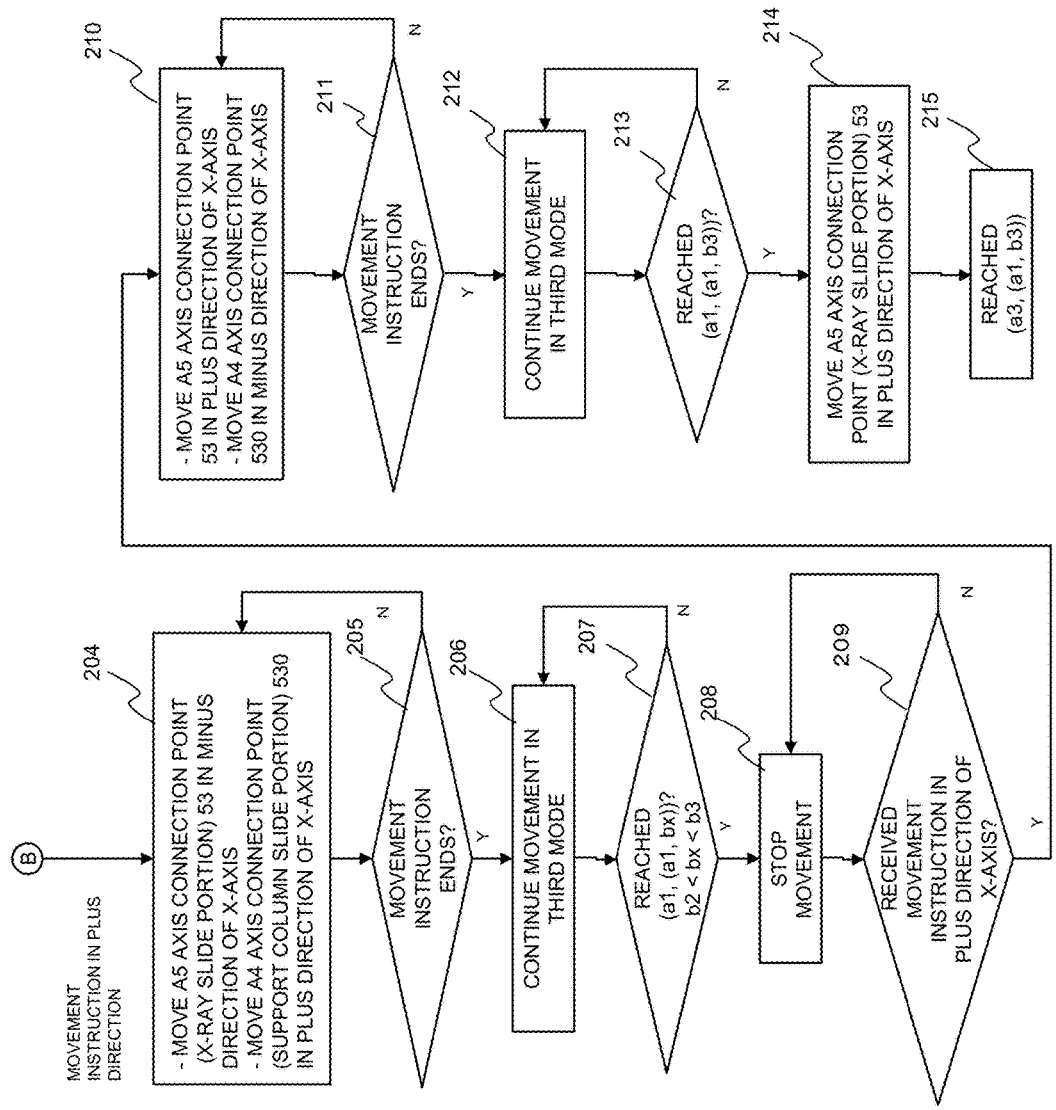
FIG. 13 is a flowchart illustrating the control operation of the device controller 120 of Embodiment 2 of the X-ray fluoroscopic imaging apparatus 1.

In Step s7 of FIG. 8, when the operation unit 122 has received the instruction to move the imaging position in the x-axis direction by the imaging technician W1, the device controller 120 proceeds to Step s8 and performs the flow of FIGS. 12 and 13.

Step 191

First, the device controller 120 determines whether the movement direction received in Step s7 is the plus direction (+x direction: direction approaching the stand 10) or the minus direction (−x direction: direction away from the stand 10) of the x-axis. If the received movement direction is the −x direction, it proceeds to Step 192 in FIG. 12. If the received movement direction is the +x direction, it proceeds to Step 204 in FIG. 13.

Step 192

In Step 192, the device controller 120 operates the first slide mechanism 51m to move the support column slide portion 530 on which the support column 50 is mounted in the −x direction at the first speed v1, while moving the X-ray slide portion (A5 axis connection point) 53 at the second speed v2 in the +x direction opposite to the −x direction in which the operation unit 122 has received the movement instruction. Note that the device controller 120 sets the first speed v1 to be larger than the second speed v2 (second mode). However, the configuration is not limited to the movement in the second mode, and the device controller 120 may operate the motor 512 of the second slide mechanism 52m to move the X-ray slide portion (A5 axis connection point) 53 in the −x direction with respect to the guide rail 511 (first mode). Thus, the X-ray generator 60 and the X-ray support arm 90 move in the −x direction with respect to the upper end of the support column 50 (movement from II-00 to II-11 in FIG. 11).

Steps 193-195

When the movement instruction from the user is completed, the movement is continued in the third mode (Steps 193 and 194) (II-12). In the third mode, the device controller 120 operates the first slide mechanism 51m to move the support column slide portion 530 on which the support column 50 is mounted in the −x direction at a third speed v3, while moving the X-ray slide portion (A5 axis connection point) 53 at a fourth speed v4 in the +x direction opposite to the −x direction in which the operation unit 122 has received the movement instruction. Note that the device controller 120 does not move the position of the X-ray generator 60 but moves the support column 50 in the −x direction, by setting the third speed v3 and the fourth speed v4 to the same speed.

In Step 195, the device controller 120 determines whether the X-ray slide portion (A5 axis connection point) 53 has reached the position a3 of the end of the guide rail 511 based on the drive amount of the motor 512, and the position a3 of the end of the guide rail 511 has reached a position bx (b1<bx<b2) of the support column guide rail 501 (positional relationship (a3, (a3, bx)) shown by II-12 in FIG. 14), and if so, the device controller 120 proceeds to Step 196 and stops the movement.

If not, the device controller 120 returns to Step 194 and continues the movement in the third mode.

Steps 197 and 198

In Step 197, when the operation unit 122 has received the movement instruction in the minus direction of the X axis from the user, the device controller 120 proceeds to Step 198 and operates the motor 512 of the second slide mechanism 52m to move the X-ray slide portion (A5 axis connection point) 53 with respect to the guide rail 511 in the −x direction at a fifth speed v5 (first mode). At this time, the device controller 120 may operate the first slide mechanism 51m to move the support column slide portion 530 on which the support column 50 is mounted in the +x direction at a sixth speed v6 (II-13 in FIG. 14). In this case, the device controller 120 sets the fifth speed v5 to be larger than the sixth speed v6.

Steps 199 to 201

When the movement instruction from the user is completed, the movement is continued in the third mode (Step 200). The third mode is the same as in Step 194.

In Step 201, the device controller 120 determines whether the X-ray slide portion (A5 axis connection point) 53 has reached the position a2 of the end of the guide rail 511 based on the drive amount of the motor 512, and the position a3 of the end of the guide rail 511 has reached the end b1 of the support column guide rail 501 (positional relationship (a2, (a3, b1)) shown by II-14 in FIG. 14), and if so, it proceeds to Step 202.

As illustrated in II-14 of FIG. 14, since the position a3 of the end of the guide rail 511 has reached the end b1 of the support column guide rail 501 at this point, in Step 202, the device controller 120 moves only the X-ray slide portion (A5 axis connection point) 53 in response to the instruction from the user by a joystick operation or the like, thereby moving the X-ray generator 60 to a desired position as shown by II-15 in FIG. 14, and finally to (a1, (a3, b1)) shown by II-16 in FIG. 14 (Steps 202 and 203).

Steps 204 to 215

If the movement direction received by the operation unit 122 is the +x direction in Step 191 described above, Steps 204 to 215 are performed to move the X-ray detector 60 in the +x direction.

As described above, in Embodiment 2, the X-ray slide portion (A5 axis connection point) 53 and the support column slide portion 530 are moved by the first mode or the second mode according to the movement instruction from the user. Thereafter, even after the movement instruction from the user is stopped, by moving the support column 50 in the direction instructed by the user by moving the X-ray slide portion (A5 axis connection point) 53 and the support column slide portion 530 in the third mode without changing the position of the X-ray generator 60, when the next movement instruction is received, the X-ray generator 60 can be moved to a target position by moving the X-ray slide portion (A5 axis connection point) 53.

Note that in the third mode, since the X-ray slide portion (A5 axis connection point) 53 and the support column slide portion 530 are moved without the instruction by the user, when the user performs imaging or fluoroscopy, the movement is stopped in the third mode. For example, the device controller 120 stops the third mode when anode rotation of the X-ray generator 60 is started. Note that in the case of fluoroscopy, it is also possible to allow the movement in the third mode.

Embodiment 3

In Embodiment 3, when the operation unit 122 is an operation unit, for example, such as a joystick having a function of receiving an instruction of fine adjustment mode α or high-speed mode β from the user, and the movement speed received by the operation unit 122 is the high-speed mode β, the device controller 120 preferentially performs the second mode to move the support column 50 in the direction instructed by the user, while moving the X-ray slide portion (A5 axis connection point) 53 in the opposite direction. Thus, the X-ray generator 60 can be quickly reached the position desired by the user, and the final fine adjustment can be performed by moving only the X-ray slide portion (A5 axis connection point) 53.

Hereinafter, the control operation of the device controller 120 of Embodiment 3 will be specifically described with reference to a flow of FIGS. 15 and 16 and FIG. 17.

As in FIG. 11, FIG. 17 is a diagram schematically illustrating the positional relationship between the support column guide rail 501 fixed to the support column support arm 20 and the support column slide portion 530 equipped with the support column 50 and sliding on the support column guide rails 501, and the positional relationship between the X-ray guide rail 511 fixed to the upper end of the support column 50 and the X-ray slide portion 53 that slides on the X-ray guide rails 511 together with the X-ray generator 60 and the X-ray support arm 90. "III-00" in FIG. 17 is the initial state like "I-00" in FIG. 11.

In Step s7 of FIG. 8, when the operation unit 122 has received the instruction to move the imaging position in the x-axis direction by the imaging technician W1, the device controller 120 proceeds to Step s8 and performs the flow of FIGS. 15 and 16.

Step 251

First, the device controller 120 determines whether the movement direction received in Step s7 is the plus direction (+x direction: direction approaching the stand 10) or the minus direction (−x direction: direction away from the stand 10) of the x-axis. If the received movement direction is the −x direction, it proceeds to Step 252 in FIG. 15. If the received movement direction is the +x direction, it proceeds to Step 262 in FIG. 16.

Step 252

In Step 252, the device controller 120 determines whether the speed instructed by the operation unit 122 such as the joystick is the high-speed mode β or the fine adjustment mode α, and if the speed is the fine adjustment mode, the positional relationships shown in III-00, III-12, and III-13 in FIG. 17 are sequentially reached by performing Steps 132 to 135.

After Step 135, in Step 257, the device controller 120 again determines whether the speed instructed by the operation unit 122 such as the joystick is the high-speed mode β or the fine adjustment mode α, and if the speed is the fine adjustment mode α, the positional relationships shown in III-15, III-16, and III-17 in FIG. 17 are reached by performing Steps 136 to 141.

Since Steps 132 to 135 and 136 to 141 are the same operations as those in Embodiment 1, description thereof will be omitted here.

On the other hand, in Step 252, the device controller 120 proceeds to Step 253 when the speed instructed by the operation unit 122 such as the joystick is the high-speed mode β.

Step 253

In Step 253, the device controller 120 operates the first slide mechanism 51m to move the support column slide portion 530 on which the support column 50 is mounted in the −x direction at the first speed v1, while moving the X-ray slide portion (A5 axis connection point) 53 at the second speed v2 in the +x direction opposite to the −x direction in which the operation unit 122 has received the movement instruction. Note that the device controller 120 sets the first speed v1 to be larger than the second speed v2 (second mode). Thus, the X-ray generator 60 and the X-ray support arm 90 move in the −x direction with respect to the upper end of the support column 50, and the high-speed mode β in which the support column 50 is moved in the −x direction is started (III-11 in FIG. 17).

Step 254

The device controller 120 determines whether the X-ray slide portion (A5 axis connection point) 53 has reached a predetermined position R3 (see III-11 in FIG. 17) between the positions a2 and a3 of the guide rail 511, and if the X-ray slide portion has reached the position R3, it proceeds to Step 255.

Step 255

In Step 255, the device controller 120 moves the X-ray slide portion (A5 axis connection point) 53 in the −x direction in which the operation unit 122 has received the movement instruction. (In addition, it moves the support column slide portion 530 in the +x direction.)

Step 256

In Step 256, the device controller 120 determines whether the X-ray slide portion (A5 axis connection point) 53 has reached the center position a2 of the guide rail 511, and the center position a2 of the guide rail 511 has reached the end b1 of the support column guide rail 501 (positional relationship (a2, (a2, b1)) shown by I-12 in FIG. 11), and if so (III-13 in FIG. 17), it proceeds to Step 257.

Step 257

In Step 257, the device controller 120 again determines whether the speed instructed by the operation unit 122 such as the joystick is the high-speed mode β or the fine adjustment mode α, and if the speed is the fine adjustment mode α, it performs Steps 136 to 141 as described above. On the other hand, when the high-speed mode β is instructed, it proceeds to Step 258.

Step 258

In Step 258, as in Step 253, the device controller 120 moves the support column slide portion 530 in the −x direction at the first speed v1, while moving the X-ray slide portion (A5 axis connection point) 53 at the second speed v2 in the +x direction opposite to the −x direction in which the operation unit 122 has received the movement instruction. Note that the device controller 120 sets the first speed v1 to be larger than the second speed v2 (second mode). Thus, the X-ray generator 60 and the X-ray support arm 90 move in the −x direction with respect to the upper end of the support column 50, and the support column 50 moves in the −x direction (III-14 in FIG. 17).

Step 259

The device controller 120 determines whether the X-ray slide portion (A5 axis connection point) 53 has reached the predetermined position R3 (see III-14 in FIG. 17) between the positions a2 and a3 of the guide rail 511, and if so, it proceeds to Step 260.

Step 260

In Step 260, the device controller 120 moves the X-ray slide portion (A5 axis connection point) 53 in the −x direction in which the operation unit 122 has received the movement instruction. In addition, it moves the support column slide portion 530 in the +x direction.

Step 261

The device controller 120 determines whether the X-ray slide portion (A5 axis connection point) 53 has reached the predetermined position R1 (see I-11 in FIG. 11) between the positions a1 and a2 of the guide rail 511, and if the X-ray slide portion has reached the position R1, it proceeds to Step 262. If the X-ray slide portion has not reached the position R1, it returns to Step 260 to continue the movement.

Steps 262 and 263

In Step 262, the device controller 120 moves the X-ray slide portion (A5 axis connection point) 53 in the −x direction in which the operation unit 122 has received the movement instruction. In addition, the device controller 120 moves the support column slide portion 530 in the −x direction. The device controller 120 ends when the positional relationship between the X-ray slide portion (A5 axis connection point) 53 and the support column slide portion 530 reaches (a1, (a3, b1)) (III-17 in FIG. 17).

Steps 264 to 273

In Step 251 described above, when the movement direction received by the operation unit 122 is the +x direction, Steps 264 to 273 and 142 to 151 in FIG. 16 are performed to move the X-ray detector 60 in the +x direction.

As described above, in Embodiment 3, the fine adjustment mode α and the high-speed mode β can be selectively performed, and in the fine adjustment mode α, the movement of the X-ray generator 60 can be started and stopped smoothly with a quick reaction by the movement of the X-ray slide portion (A5 axis connection point) 53 as in Embodiment 1. On the other hand, in the high-speed mode β, by preferentially performing the second mode, the X-ray generator 60 can be quickly reached the position desired by the user, and the final fine adjustment can be performed by moving only the X-ray slide portion (A5 axis connection point) 53.

Note that in Step 257 in the middle of the flow, the user can switch between the high-speed mode β and the fine adjustment mode α.

What is claimed is:

1. An X-ray fluoroscopic imaging apparatus comprising:
a stand placed on a floor surface;
a support column support arm projecting from one side of the stand in a predetermined direction;
a support column having a lower end mounted on the support column support arm, and supported by the support column support arm;
an X-ray support arm projecting from an upper end of the support column in a direction parallel to the predetermined direction;
an X-ray generator supported by the X-ray support arm;
a first slide mechanism that is disposed between the support column support arm and the lower end of the support column and slides the lower end of the support column parallel to the predetermined direction with respect to the support column support arm;
a second slide mechanism that is disposed between the upper end of the support column and the X-ray support arm and slides the X-ray support arm parallel to the predetermined direction with respect to the upper end of the support column;
a controller that controls operations of the first and second slide mechanisms; and
an operation unit that receives an instruction from a user to move the X-ray generator in the predetermined direction, wherein
when the operation unit has received the instruction from the user to move the X-ray generator in the predetermined direction,
the controller performs the following first mode and second mode in order,
the first mode in which the controller operates the second slide mechanism to move the X-ray support arm in the predetermined direction with respect to the upper end of the support column, so that the X-ray generator is moved to the predetermined direction, and
the second mode in which the controller operates the first slide mechanism to move the lower end of the support column at a predetermined first speed in the predetermined direction with respect to the support column support arm, while operating the second slide mechanism to move the X-ray support arm at a second speed smaller than the first speed in a direction opposite to the predetermined direction with respect to the upper end of the support column, so that the X-ray generator is moved in the predetermined direction.

2. The X-ray fluoroscopic imaging apparatus according to claim 1, wherein the controller performs the second mode when the X-ray generator reaches a predetermined position in a movable range of the second slide mechanism in the first mode.

3. The X-ray fluoroscopic imaging apparatus according to claim 1, wherein
the controller performs a third mode when a movement instruction from the user is stopped after the first mode or the second mode, and
in the third mode, the controller moves the lower end of the support column at a third speed with respect to the support column support arm in a direction instructed by the user to move in the first mode or the second mode performed immediately before, while moving the X-ray support arm at a fourth speed equal to the third speed in a direction opposite to the direction instructed by the user with respect to the upper end of the support column.

4. The X-ray fluoroscopic imaging apparatus according to claim 1, wherein
the operation unit has a function of receiving an instruction from the user to select a low-speed movement mode or a high-speed movement mode, and
when the operation unit has received the high-speed movement mode, the controller performs the second mode with priority over the first mode.

5. The X-ray fluoroscopic imaging apparatus according to claim 1, further comprising an imaging switch that allows the user to instruct fluoroscopic imaging and X-ray imaging, wherein
the controller stops performing the first and second modes at least when the X-ray imaging is instructed.

6. The X-ray fluoroscopic imaging apparatus according to claim 3, wherein the controller stops the third mode when anode rotation of the X-ray generator is started.

* * * * *